(12) United States Patent
Endou et al.

(10) Patent No.: US 8,039,586 B1
(45) Date of Patent: Oct. 18, 2011

(54) CEREBRAL ORGANIC ANION TRANSPORTER AND ITS GENE

(75) Inventors: Hitoshi Endou, Sagamihara (JP); Takashi Sekine, Tachikawa (JP); Hiroyuki Kusuhara, Tokyo (JP)

(73) Assignee: J-Pharma Co., Ltd., Tokyo (JP)

( * ) Notice: Subject to any disclaimer, the term of this patent is extended or adjusted under 35 U.S.C. 154(b) by 0 days.

(21) Appl. No.: 09/787,194

(22) PCT Filed: Sep. 20, 1999

(86) PCT No.: PCT/JP99/05120
§ 371 (c)(1),
(2), (4) Date: Sep. 6, 2007

(87) PCT Pub. No.: WO00/17237
PCT Pub. Date: Mar. 30, 2000

(30) Foreign Application Priority Data

Sep. 18, 1998 (JP) .................................... 10/265126

(51) Int. Cl.
*C07K 14/705* (2006.01)
(52) U.S. Cl. ...................................................... 530/350
(58) Field of Classification Search .................. None
See application file for complete search history.

(56) References Cited

FOREIGN PATENT DOCUMENTS

| WO | WO 97/42321 | 11/1997 |
|---|---|---|
| WO | WO 01/04283 | 1/2001 |

OTHER PUBLICATIONS

T. Sekine et al., "Expression Cloning and Characterization of a Novel Multispecific Organic Anion Transporter," J. Biol. Chem., vol. 272, No. 30, Jul. 1997, pp. 18526-18529.
C. Heaney et al., "Human autosomal recessive osteopetrosis maps to 11q13, a position predicted by comparative mapping of the murine osteosclerosis (oc) mutation," Human Mol. Genetics, 1998, vol. 7, No. 9, pp. 1407-1410.
J. Race et al., "Molecular Cloning and Characterization of Two Novel Human Renal Organic Anion Transporters (hOAT1 and hOAT3)," BioChem. & Biophys. Research Communications, 255, 1999, pp. 508-514.
K. Brady et al., "A Novel Putative Transporter Maps to the Osteosclerosis (oc) Mutation and Is Not Expressed in the Mutant Mouse," Genomics, 56, 1999, pp. 254-261.
M. Hosoyamada et al., "Molecular cloning and functional expression of a multispecific organic anion transporter from human kidney," Am. J. Physiology, vol. 276, No. 1 part 2, Jan. 1999, pp. F122-F128.
H. Endou, "Recent advances in molecular mechanisms of nephrotoxicity," Toxicology Letters, Elsevier Biomedical Press, vol. 102/103, Dec. 1998, pp. 29-33.
Kusuhara et al., "Characterization of Efflux Transport of Organic Anions in a Mouse Brain Capillary Endothelial Cell Line," The Journal of Pharmacology and Experimental Therapeutics 285:1260-1265 (1998).
Noé et al., "Isolation of a Multispecific Organic Anion and Cardiac Glycoside Transporter from Rat Brain," Proc. Natl. Acad. Sci. USA 94:10346-10350 (1997).
Endou et al. "Molecular Cloning and Characterization of a New Multispecific Organic Anion Transporter from Rat Brain", J. Biol. Chem (May 1999) p. 13675-13680.
Endou et al. "Identification of multispecific organic anion transporter 2 expressed predominantly in the liver", FEBS Letters (Jun. 1998) p. 179-182.
XP002214544—Online Search: C. Heaney et al., "Mus musculus reduced in osteosclerosis transporter (Roct) mRNA, complete cds", (1998) Database Accession No. AF078869.
XP002214546—Online Search: R. Strausberg, "Homo sapiens cDNA clone Image:2527728 3' similar to TR:088909 088909 reduced in osteosclerosis transporter; mRNA sequence", (1999), Database Accession No. AW025165.
XP002214545—Online Search: R. Strausberg et al., "Homo sapiens cDNA clone Image:1323232 3', mRNA sequence", (1998), Database Accession No. AA877205.
XP002225616—Online Search: M. Marra et al., "Mus musculus cDNA clone Image: 572103 5' similar to TR: G1293672 G1293672 Kidney-specific transport protein; mRNA sequence", (1996), Database Accession No. AA108584.
Partial European Search Report for EP 99 94 3423 dated Oct. 16, 2002.
Supplmentary European Search Report for EP 99 94 3423 dated Jan. 22, 2003.

*Primary Examiner* — John Ulm
(74) *Attorney, Agent, or Firm* — Peter F. Corless; Christine C. O'Day; Edwards Angell Palmer & Dodge LLP

(57) ABSTRACT

A cerebral organic anion transporter OAT3 which is useful as a protein regulating the uptake/excretion of organic anionic substances in the brain; a nucleic acid having a base sequence encoding the same; and an antibody against the same. The amino acid sequence and the base sequence of the above OAT3 are shown in Sequence Listing in the description.

1 Claim, 13 Drawing Sheets

Dehydroepiandrosterone sulfate (50 nM)

Ochratoxin A (100 nM)

CEREBRAL ORGANIC ANION TRANSPORTER AND ITS GENE

TECHNICAL FIELD

The present invention relates to a gene involved in organic negative ion (organic anion) transport and the polypeptide encoded by the gene.

BACKGROUND ART

Liver and kidney play important roles in the metabolism and excretion of biologically foreign compounds and drugs out of bodies. Tubule cells and hepatocytes belong to epithelial cells with polarities. It is supposed that some of anionic substances are taken up through the basolateral membranes into kidney and liver by transporters, while the organic anions generated metabolically in cells are excreted by transporters.

The uptake of organic anions through the basolateral membranes of tubule cells and hepatocytes have been investigated so far in experiment systems using isolated organ perfusion protocols, dissected cells and membrane vesicles. According to such conventional methods, however, the detailed analysis of the transport of organic anions through the basolateral membranes has been difficult. Accordingly, it has been desired to isolate the transporters per se and analyze the properties of transporters in detail.

Alternatively, plural experimental results suggestively indicate the presence of the transport of organic anions in brain. The transport of organic anions in brain is supposed to function for the extracerebral excretion of endogenous and exogenous organic anions.

Although the transport of organic anions in brain is speculated to play an important role in the elimination of endogenous anions and foreign compounds from brain, the detail of the transport therein is more ambiguous than the transport in kidney and liver, due to the difficulty in physiological experiments therein.

Based on these backgrounds, the screening of the organic anion transporter molecules per se has been actively carried out in 1990 and thereafter. Consequently, two organic anion transporters derived from the basolateral membrane of liver have been isolated until the last year. (Hagenbuch, B. et al., Proc. Natl. Acad. Sci. USA, Vol. 88, pp. 10629-33, 1991; Jacquemin, E. et al., Proc. Natl. Acad. Sci. USA, Vol. 91, pp. 133-7, 1994)

The present inventors independently isolated an organic anion transporter OAT1 responsible for the most important function in the organic anion transport in kidney successfully last year (Sekine, T., et al., J. Biol. Chem., Vol. 272, pp. 18526-9, 1997) and already filed the patent application thereof. OAT1 is a transporter capable of transporting a great number of organic anions with different chemical structures and is also involved in the transport of various anionic drugs. OAT1 is expressed in a specific manner to kidney, while OAT1 is very slightly expressed in brain except kidney.

Recently, the inventors have further identified a liver-specific organic anion transporter (OAT2) with about 40% homology to OAT1 in terms of amino acid level (FEBS letter, Vol. 429, pp. 179-182, 1998) (Japanese Patent Application No. 169174/1998).

The isolation and identification of OAT1 and OAT2 indicates that these organic anion transporters form a family. Additionally because OAT2 is expressed specifically in liver, it is suggested that the family is not kidney-specific but is expressed in various organs.

As described insofar, it is suggested that an organic anion transport system is present in brain, but the OAT1 expression in brain is quite slight while OAT2 is not present therein. Based on these findings, the inventors have anticipated the presence of an unknown transporter responsible for the organic anion transport in brain.

Alternatively, the organic anion transport in the basolateral membrane of liver is complicated; particularly, the efflux flow of conjugated substances (many of the conjugated substances are organic anions) generated at a vast scale in hepatocytes into blood has not yet been known. The organic anion transport in liver cannot sufficiently be described on the single basis of the organic anion transporters including OAT2. Hence, the presence of an unknown transporter is suggested.

The inventors isolated the organic anion transporter OAT1 serving as the most important role in the organic anion transport in kidney (Sekine, T. et al., J. Biol. Chem. Vol. 272, pp. 18526-9, 1997). Based on the structural similarity to OAT1, the inventors identified a liver-specific organic anion transporter (OAT2) (Sekine, T., at al., FEBS letter, Vol. 429, pp. 179-182, 1998). The inventors already reported additionally (Sekine, T., at al., J. Biol. Chem., Vol. 272, pp. 18526-9, 1997) that OAT1 had low homology to an organic cation transporter OCT1 (Grundemann, D. et al., Nature, Vol. 372, pp. 549-52, 1994).

Taking account of these evidence, the inventors identified a sequence common to OAT1, OAT2 and OCT1 and prepared a degenerate primer based on the sequence. By using the degenerate primer, the inventors identified a novel cDNA fragment with low homology to OAT1, OAT2 and OCT1 from rat brain mRNA by RT (reverse transcript)-PCR (polymerase chain reaction) method. By using the cDNA fragment, a cDNA never reported yet was discriminated from the rat cDNA library. The resulting protein was designated cerebral type organic anion transporter OAT3 as a third member of the OAT family.

DISCLOSURE OF THE INVENTION

The invention relates to the organic anion transporter OAT3. The inventive organic anion transporter OAT3 is a transporter with a wide range of substrate selectivity and transports organic anions with different chemical structures (having a potency to take up the organic anions). However, no substantial uptake of a typical organic cation TEA (tetraethylammonium) is observed. Hence, the inventive organic anion transporter OAT3 with a wide range of substrate selectivity is an organic anion transporter with no substantial substrate selectivity of TEA (tetraethylammonium) as the typical organic cation but is selectively distributed in organs mainly including brain and liver.

The inventive protein includes the organic anion transporter OAT3 of an amino acid sequence represented by SQ ID No. 2 (in human) or 4 (in rat) or of an amino acid sequence with such a modification of the aforementioned amino acid sequence as deletion, substitution or addition of one or several amino acids. The deletion, substitution or addition of amino acids is satisfactory at an extent such that no organic anion transport activity is deteriorated; the number of the amino acids then is generally 1 to about 110, preferably 1 to about 55. Such protein has generally 60 to 80%, preferably 70 to 90% homology in amino acid sequence to the amino acid sequence represented by SQ ID No. 2 or 4.

Furthermore, the invention encompasses a nucleic acid, preferably DNA or RNA, encoding the inventive protein comprising the organic anion transporter OAT3. The inventive nucleic acid encompasses the nucleic acid encoding the inventive protein and nucleic acids hybridizable with the nucleic acid under stringent conditions.

Still furthermore, the invention relates to a partial sequence of the nucleic acid encoding the inventive protein or nucleotides hybridizable with the partial sequence under stringent conditions.

Still yet furthermore, the invention relates to an antibody against the inventive protein or a polypeptide immunologically identical to the inventive protein.

BEST MODE FOR CARRYING OUT THE INVENTION

Figure 1:
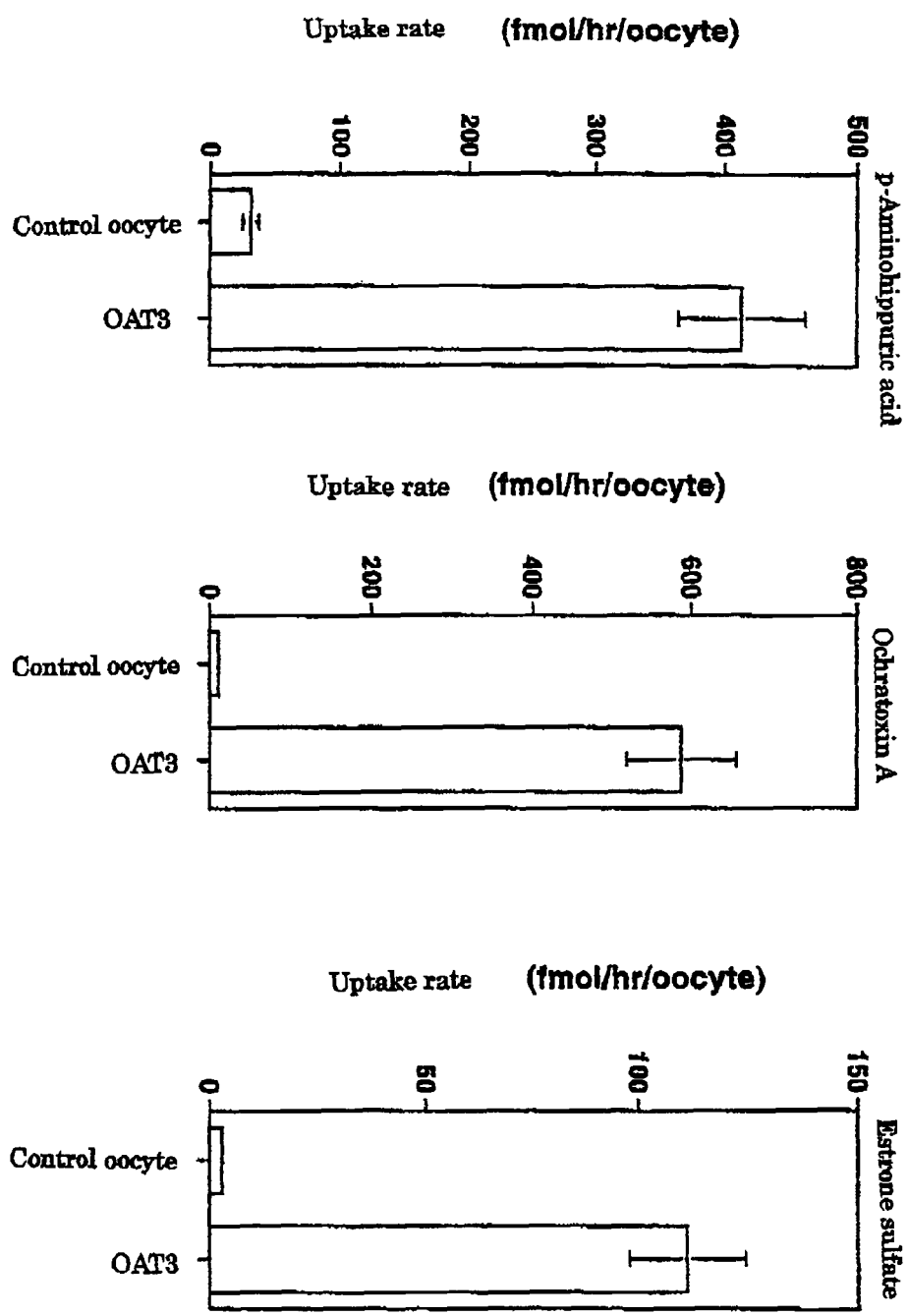
FIG. 1 depicts the organic anion uptake activity of the inventive rat OAT3 expressed in *Xenopus* oocyte.

The inventive organic anion transporter gene can be isolated and identified by screening of tissues and cells of organs such as kidney and brain in appropriate mammalian animals used as gene sources. The mammalian animals include non-human animals such as dog, cow, horse, goat, sheep, monkey, pig, rabbit, rat and mouse and additionally include human.

The gene screening and isolation can preferably be carried out by homology screening and PCR screening. The base sequence of the resulting cDNA is determined by a conventional method; the translation region is analyzed; and the amino acid sequence of the protein encoded by the cDNA, namely the amino acid sequence of OAT3, can be determined.

It is verified for example by the following manners that the resulting cDNA is the cDNA of the organic anion transporter gene, namely that the genetic product encoded by the cDNA is the organic anion transporter. More specifically, the cRNA prepared from the isolated OAT3 gene is integrated and expressed in the oocyte; then, the transport (uptake) potency of organic anions in cells is confirmed by assaying the incorporation of an appropriate organic anion as the substrate in cells by the general uptake experiment (Sekine, T., et al., J. Biol. Chem., Vol. 272, pp. 18526-9, 1997).

By applying the same uptake experiment to the expression cell, the transport property and substrate specificity of OAT3 can be examined.

The SQ ID No. 3 in the sequence listing shows the base sequence of the cDNA of the rat organic anion transporter OAT3 isolated by such method; and SQ ID No. 4 shows the amino acid sequence thereof.

By using the cDNA of the resulting OAT3 gene for screening an appropriate cDNA library or genomic DNA library prepared by using a different gene source, a homologous gene or chromosomal gene derived from a different tissue or a different biological organism or the homology can be isolated.

The base sequence of the cDNA of human organic anion transporter OAT3 identified by such method is shown as SQ ID No. 1 and the amino acid sequence thereof is shown as SQ ID No. 2.

By using a synthetic primer designed on the basis of the base sequence as the base sequence (SQ ID No. 1 or 3) of the inventive gene disclosed or a part of the information thereof the gene can be isolated from the cDNA library by general PCR.

DNA libraries such as cDNA library or genomic DNA library or the like can be prepared by the method described in for example "Molecular Cloning; Sambrook, J., Fritsh, E. F. and Maniatis, T. ed., issued by Cold Spring Harbor Laboratory Press in 1989". Otherwise, any existing commercially available library can satisfactorily be used.

The inventive organic anion transporter (OAT3) can be generated by using for example cDNA encoding the organic anion transporter by genetic recombinant technology. For example, DNA (cDNA and the like) encoding the organic anion transporter is integrated in an appropriate expression vector; and the resulting recombinant DNA can then be transfected in an appropriate host cell. The expression system (host vector system) for polypeptide generation includes for example expression systems of bacteria, yeast, insect cells and mammalian cells. Among them, insect cells and mammalian cells are preferably used for the recovery of the functional protein.

For the expression of the polypeptide in mammals, for example, the DNA encoding the inventive organic anion transporter is inserted in the downstream of an appropriate promoter (for example, SV40 promoter, LTR promoter, elongation 1α promoter and the like) in an appropriate expression vector (for example, retrovirus vector, papilloma virus vector, vaccinia virus vector, SV40 vector and the like) to construct an expression vector. By subsequently transforming an appropriate animal cell with the resulting expression vector and culturing the transformant in an appropriate culture medium, the objective polypeptide can be generated. The mammalian cell as the host includes monkey COS-7 cell, Chinese hamster CHO cell, human HeLa cell, or cell lines such as kidney tissue-derived primary culture cell, porcine kidney-derived LLC-PK1 cell and opposum kidney-derived OK cell and the like.

As the cDNA encoding the organic anion transporter OAT3, use can be made of cDNA with the base sequence represented by SQ ID No. 1 or 3; as the cDNA, with no specific limitation to the cDNA described above, additionally, DNA corresponding to the amino acid sequence is designed and used, which can encode the polypeptide. In this case, it is known that each amino acid is encoded by one to 6 types of codons, so codons for use can be selected appropriately. For example, a sequence with higher expression can be designed, in terms of the frequency of codons used by a host for expression. DNA with the designed base sequence can be recovered by chemical DNA synthesis, fragmentation and conjugation of the cDNA, and a partial modification of the base sequence. An artificial partial modification of the base sequence or mutagenesis thereof can be carried out by site specific mutagenesis, by utilizing a primer comprising a synthetic oligonucleotide encoding the desired modification "Mark, D. F., et al., Proc. Natl. Acad. Sci. USA, Vol. 8, pp. 5662-5666, 1984".

Nucleotides (oligonucleotide or polynucleotide) hybridizable with the inventive organic anion transporter gene under stringent conditions can be used as probe for detecting the organic anion transporter gene and can also be used for example as antisense oligonucleotide, ribozyme and decoy, so as to modify the expression of the organic anion transporter.

In accordance with the invention, the term hybridization under stringent conditions generally means hybridization in 5×SSC or a hybridization solution at a salt concentration equal to the concentration under a temperature condition of 37 to 42° C. for about 12 hours, followed by preliminary rinsing in 5×SSC or a solution at a salt concentration equal to the concentration and rinsing in 1×SSC or at a salt concentration equal to the concentration. Higher stringency can be realized by carrying out rinsing in 0.1×SSC or a solution at a salt concentration equal to the concentration.

Additionally, the invention relates to a partial sequence of the nucleic acid encoding the inventive protein or nucleotides hybridizable with the sequence under stringent conditions. As such nucleotides, generally, use can satisfactorily be made of nucleotides comprising a partial sequence of consecutive 14 or more nucleotides in series in the base sequence represented by SQ ID No. 1 or 3 or a sequence complementary to the partial sequence; so as to enhance the specificity of the hybridization, a longer sequence, for example a sequence of 20 bases or more or a sequence of 30 bases or more, can satisfactorily be used as such partial sequence. These nucleotides can be labeled, if necessary, with radioactive elements, fluorescent substances or chemiluminescent substances.

The nucleotides comprising a partial sequence of consecutive 14 or more base in series in the inventive base sequence represented by SQ ID No. 1 or 3 or a sequence complementary to the partial sequence preferably carries the specific base sequence of the base sequence encoding the inventive organic anion transporter OAT3 and can satisfactorily be labeled, if necessary.

By using the inventive organic anion transporter or a polypeptide immunologically identical thereto, additionally, an antibody can be raised. The antibody can be utilized for detecting or purifying the organic anion transporter. The antibody can be raised, by using the inventive organic anion transporter, a fragment thereof, or a synthetic peptide with a partial sequence thereof or the like as an antigen. The antibody, if polyclonal, can be generated by general methods comprising inoculating such antigen in a host animal (for example, rat and rabbit) and recovering the resulting immunized serum. The antibody, if monoclonal, can be generated by techniques such as general hybridoma method. Further, the inventive antibody is satisfactorily prepared as chimera form or humanized antibody.

BEST MODE FOR CARRYING OUT THE INVENTION

The description is now made in more detail in the following examples, but the examples are in no way of limitation of the invention.

In the following examples, the individual procedures followed the methods described in "Molecular Cloning; Sambrook, J., Fritsh, E. F. and Maniatis, T. ed., issued by Cold Spring Harbor Laboratory Press in 1989" or followed the instructions of commercially available kit products if used, unless otherwise stated.

EXAMPLE 1

Isolation and analysis of multi-selective organic anion transporter 3 (OAT3) cDNA (1) Preparation of degenerate primer based on the base sequence information of OAT1, OAT2 and OCT1

Based on the base sequence information of OAT1 and OAT2 isolated previously by the inventors and the reported base sequence information of OCT1, degenerate primer was prepared with reference to amino acid sequences in common to these three transporters (amino acids 267-275 and amino acids 447-452 in the amino acid sequence of OAT1).

From rat brain was extracted total RNA by GITC method; and poly(A)+RNA was then purified by using an oligodT column. From the rat brain poly(A)+RNA was prepared cDNA by using reverse transcriptase; using the resulting cDNA as template, PCR was conducted with the degenerate primer. Consequently, a PCR product of about 550 bp was prepared.

By using a TA cloning kit (manufactured by Invitrogen Co.), the PCR product was cloned; and some of the base sequence was determined. Consequently, a novel cDNA (B10) with homology at the level of 50% to OAT1 in terms of amino acid level was recovered.

A probe prepared by labeling B10 cDNA with $^{32}P$ was used for Northern hybridization with poly(A)+RNA extracted from various rat organs. Positive bands were visually detected in the liver, kidney, brain and eyes.

Because the inventors had an excellent cDNA library of rat kidney, the inventors screened the rat kidney cDNA library by using the B10 probe. Hybridization was promoted overnight in a hybridization solution at 37° C. Thereafter, the filter membrane was rinsed in 0.1×SSC/0.1% SDS at 37° C. As the hybridization solution, use was made of a buffer, pH 6.5 containing 50% formamide, 5×standard saline citrate (SSC), 3×Denhard solution, 0.2% SDS, 10% dextran sulfate, 0.2 mg/ml modified salmon sperm DNA, 2.5 mM sodium pyrophosphate, 25 mM MES, and 0.01% Antifoam B (manufactured by Sigma, Co.). The clone isolated in λZipLox was further subcloned in a plasmid vector pZL by in vivo excision method. Consequently, a novel clone (rk1411) with an organic anion transport activity was recovered (Example 2 below is to be referenced concerning transport function analysis).

The base sequence of the clone (rk1411) recovered above was determined as follows. By firstly using a kilo-sequence deletion kit (manufactured by TaKaRa, Co.), plural plasmid DNAs were prepared by subjecting the clone rk1411 to each deletion of about 300 bp from the single side thereof. The base sequences of the DNAs were determined by using an automatic sequencer (manufactured by Applied BioSystems). Additionally, a specific oligonucleotide primer for rk1411 was prepared; by using the automatic sequencer, the base sequences thereof were also analyzed from the opposite direction. Finally, the whole base sequence of rk1411 was determined. The base sequence is shown as SQ ID No. 3 in the sequence listing. Additionally, the amino acid sequence of the protein is shown as SQ ID No. 4.

EXAMPLE 2

(Identification of the function of rk1411)

(1) By using T7 RNA polymerase, cRNA (RNA complementary to cDNA) was prepared in vitro from the plasmid carrying the clone (rk1411) as described above (see Sekine, T., et al. J. Biol. Chem., Vol. 272, pp. 18526-9, 1997).

According to the method already reported (Sekine, T., et al. J. Biol. Chem., Vol. 272, pp. 18526-9, 1997), the resulting cRNA was injected in the *Xenopus oocyte*; the oocyte was subjected to an uptake test with various radiolabeled organic anions and organic cations. As shown in FIG. 1, consequently, the oocyte in which rk1411 was expressed could take up $^{14}$C-PAH (p-aminohippuric acid), $^{3}$H-ochratoxin A and $^{3}$H-estrone sulfate. Alternatively, the oocyte never transported one typical organic cation $^{14}$C-TEA (tetraethylammonium).

Figure 2:
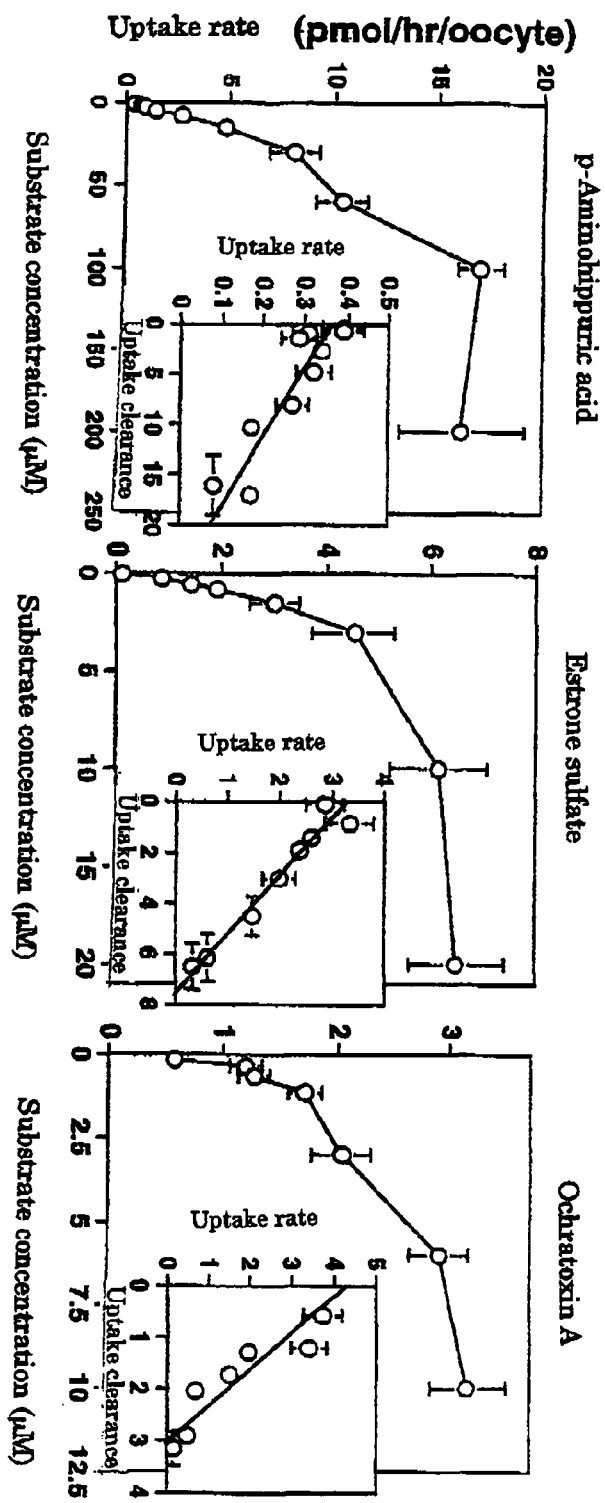
FIG. 2 depicts the results of kinetic analyses of the transport of PAH, estrone sulfate and ochratoxin A with the inventive rat OAT3 in the oocyte.

The organic anion transport with rk1411 was subjected to the Michaelis-Menten dynamic test. By examining the change in the uptake of PAH, estrone sulfate and ochratoxin A at various concentrations, the dependency of the rk1411 transport on the concentrations of these substrates was examined. The uptake experiments of radiolabeled PAH, estrone sulfate and ochratoxin A were carried out by using the oocyte injected with rk1411 cRNA according to the method described above. The results are as follows (see FIG. 2): the Km values of PAH, estrone sulfate and ochratoxin A were 4.7 µM, 2.3 µM and 0.74 µM, respectively. The results are shown below in Table 1.

TABLE 1

Results of Michaelis-Menten dynamic test

|  | Km (µM) | Vmax (pmol/hr/oocyte) | Vmax/Km (µl/hr/oocyte) |
| --- | --- | --- | --- |
| PAH | 64.7 ± 10.0 | 23.3 ± 2.8 | 0.360 |
| Estrone sulfate | 2.34 ± 0.20 | 7.60 ± 0.44 | 3.24 |
| Ochratoxin A | 0.739 ± 0.178 | 8.08 ± 0.33 | 4.17 |

Figure 3:
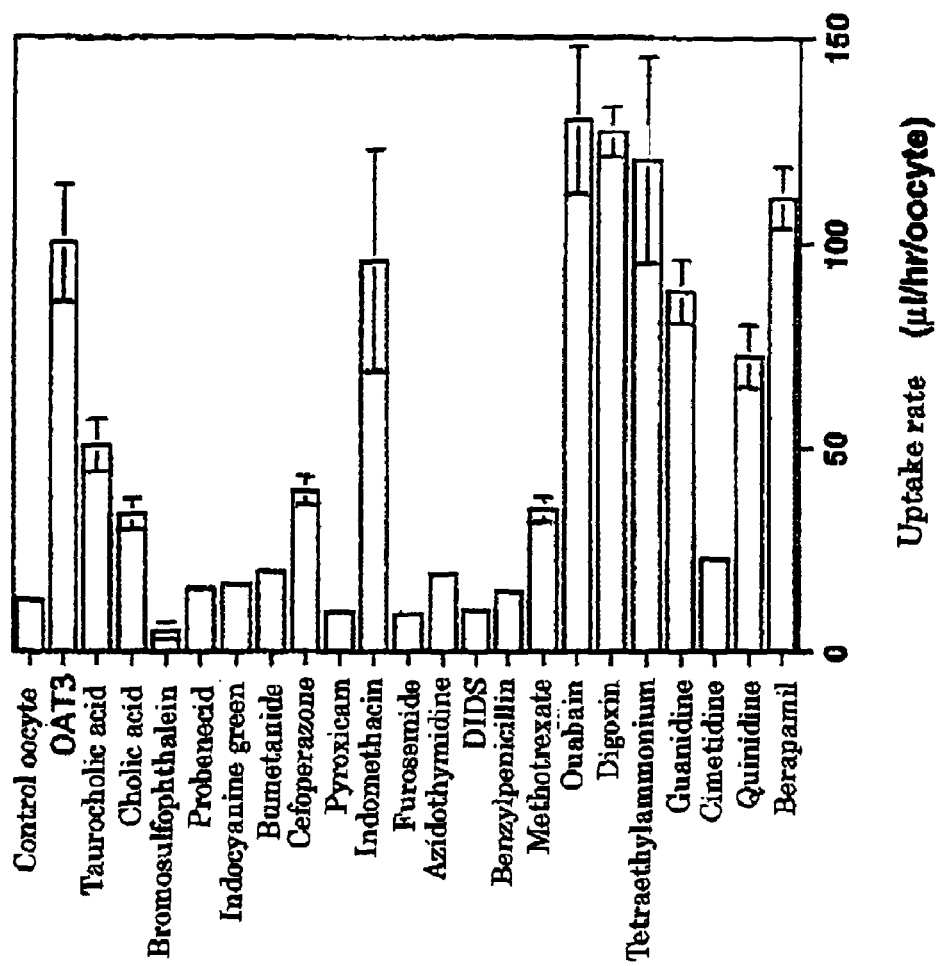
FIG. 3 depicts the results on the inhibition of the organic anion transport with the inventive rat OAT3 by various organic substances.

(2) So as to examine the substrate selectivity of rk1411, various anionic substances were added to the $^{3}$H-estrone sulfate uptake experiment system with the oocyte injected with rk1411 cRNA, to examine their influences (inhibition experiment). The $^{3}$H-estrone sulfate uptake experiment was conducted by using the oocyte injected with rk1411 cRNA according to the method described above. In the presence and absence of 1 mM each compound (with no label), the uptake of $^{3}$H-estrone sulfate was assayed. Consequently, various anionic substances (taurocholic acid, cholic acid, bromosulfophthalein, probenecid, indocyanine green, bumetanide, cefoperazone, pyroxicam, furosemide, azidothymidine, benzylpenicillin and the like) significantly inhibited the $^{3}$H-estrone sulfate transport with rk1411 (see FIG. 3). Meanwhile, cationic substances such as tetraethylammonium, guanidine, quinidine and berapamil never exerted any such inhibitory action (see FIG. 3). The results indicate that rk1411 is a multi-selective transporter and primarily recognizes organic anions. Hence, rk1411 was designated OAT3 (organic anionic transporter 3) as a third member of the OAT family.

EXAMPLE 8

The expression of the OAT3 gene in individual rat tissues was analyzed (Northern blotting). The OAT3 cDNA in the whole length was labeled with $^{32}$P-dCTP; by using the resulting cDNA as probe, RNAs extracted from various rat tissues were subjected to Northern blotting as follows. 3 µg of poly (A)+RNA was electrophoresed on 1% agarose/formaldehyde gel and subsequently transferred on a nitrocellulose filter. The filter was hybridized overnight in a hybridization solution containing the whole length of the $^{32}$-dCTP-labeled OAT3 cDNA at 42° C. The filter was rinsed in 0.1×SSC containing 0.1% SDS at 65° C.

Figure 4:
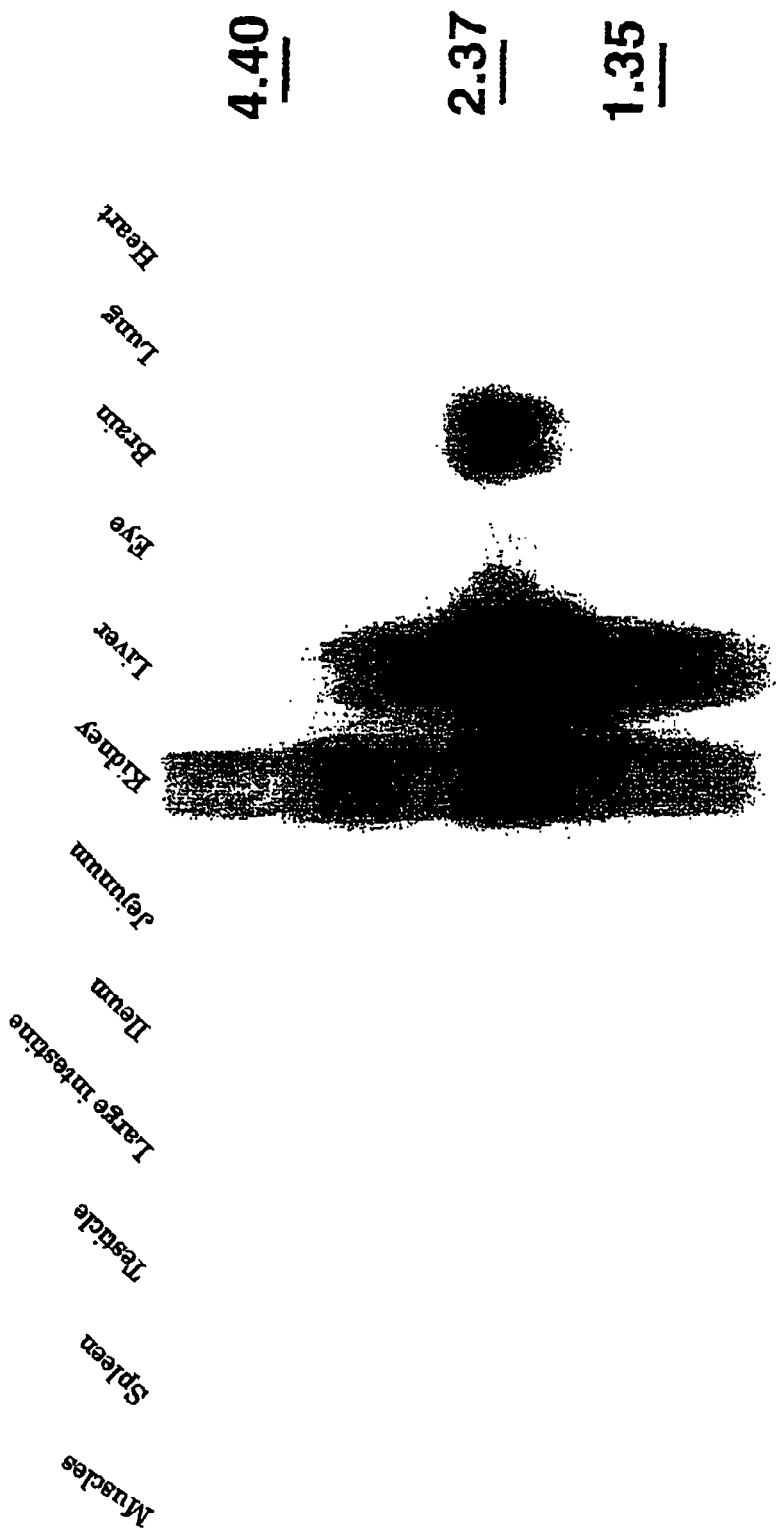
FIG. 4 depicts the results of the Northern blotting analysis of the inventive rat OAT3 gene.

The Northern blotting results (see FIG. 4) indicate that a strong band was detected around 2.4 Kb in the RNAs from the kidney, liver and brain. Visually weak expression was also observed in the eyes.

EXAMPLE 4

Figure 5:
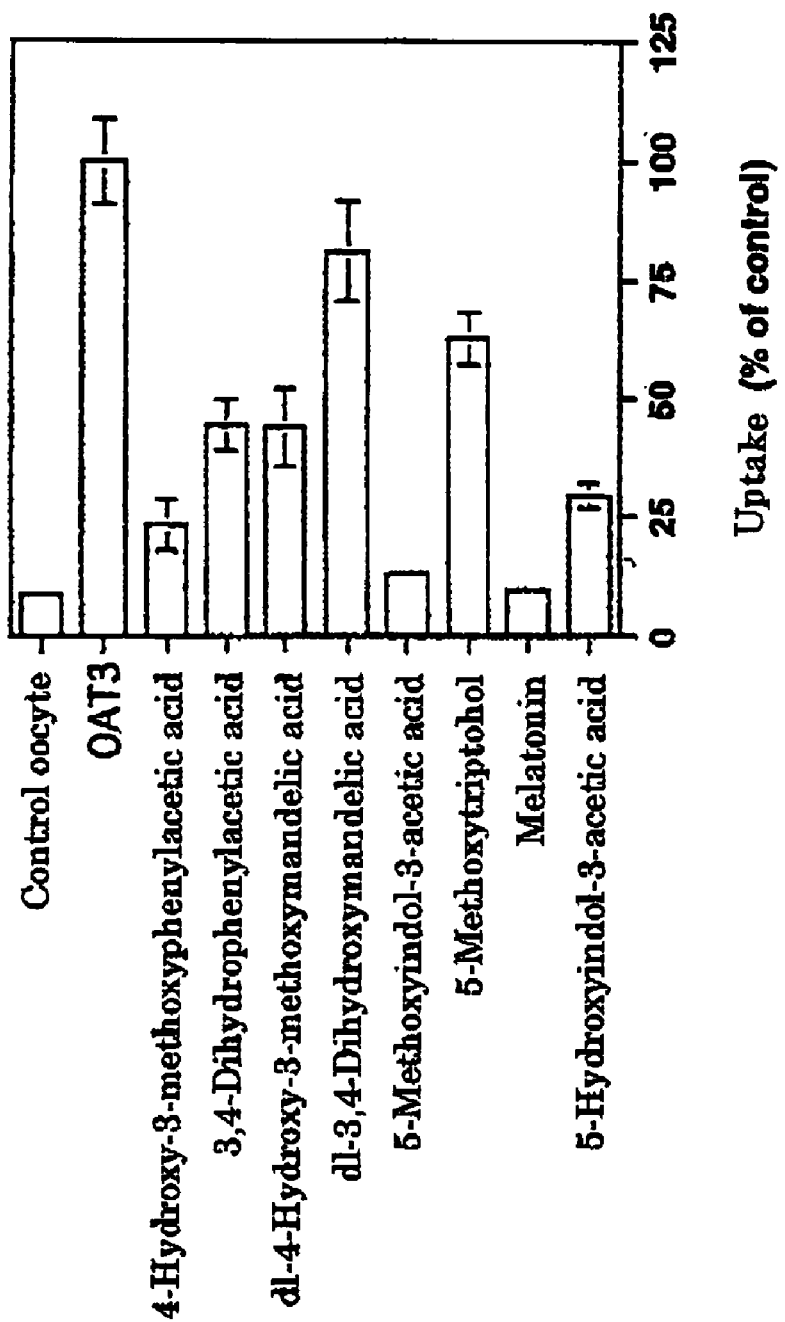
FIG. 5 depicts the results on the inhibition of the rat OAT3 transport by various metabolites of cerebral type neurotransmitters.

Because OAT3 was most strongly expressed in brain among the members of the OAT family, an attempt was made to deduce the role thereof in brain at an inhibition experiment of the OAT3 transport with various metabolites of neurotransmitters (mainly organic anions). As shown in FIG. 5, noradrenalin and serotonin metabolites inhibited the OAT3 transport of estrone sulfate, suggesting a possibility that these metabolites per se might be substrates of OAT3. The evidence indicates that OAT3 has an action to excrete neurotransmitter metabolites out of brain as one function of cerebral type OAT3.

EXAMPLE 5

Isolation and analysis of human-type multi-selective organic anion transporter 8 (OAT3) cDNA EST (expressed sequence tag) data base was screened by using the rat OAT3 cDNA isolated previously by the inventors. Human EST done (H20345) with high homology to the rat OAT3 was identified. A part (333 bp) of the base sequence of the clone was synthesized by PCR. The cDNA fragment was labeled with $^{32}$P, which was then used as probe for the following screening.

The human kidney cDNA library maintained by the inventors was subjected to screening with the probe. Hybridization was effected all day long and overnight in a hybridization solution at 37° C.; subsequently, the filter membrane was rinsed in 0.1×SSC/0.1% SDS at 37° C. As the hybridization solution, use was made of a buffer, pH 6.5, containing 50% formamide, 5×SSC (standard saline citrate), 3×Denhard solution, 0.2% SDS, 10% dextran sulfate, 0.2 mg/ml modified salmon sperm DNA, 2.5 mM sodium pyrophosphate, 25 mM MES, and 0.01% Autifoam B (manufactured by Sigma, Co.). The clone isolated in λZipLox was further subcloned in a plasmid vector pZL by in vitro excision method. Consequently, a novel human organic anion transporter 3 (hOAT3)

with an organic anion transport activity was recovered. The analysis of the transport function thereof is described below in Example 6.

The base sequence of hOAT3 was determined by the following method. Oligonucleotide primers specific to hOAT3 were sequentially synthesized. By using an automatic sequencer (manufactured by Applied BioSystems, Co.), the base sequence was analyzed, starting from both the 5'- and 3'-termini. Finally, the whole base sequence of hOAT3 was determined. The determined base sequence is shown as SQ ID No. 1 in the sequence listing. Based on the cDNA sequence, the amino acid sequence encoding hOAT3 is described as SQ ID No. 2 in the sequence listing.

The base sequence of the cDNA is shown in Table 2, while the amino acid sequence is shown in Table 3, in a corresponding manner.

TABLE 2

| Base sequence of hGAT3 cDNA | | | | | |
|---|---|---|---|---|---|
| 10 | 20 | 30 | 40 | 50 | 60 |
| CTGAGCTGCC | CTACTACAGC | AGCTGCCGGC | CCCTAGGACA | GAGCAGGGAC | CTCAACTACA |
| 70 | 80 | 90 | 100 | 110 | 120 |
| CTGATCACCA | GCCCCATCGG | ATCCAGACCC | GGCCACCAGC | TCTGGCTCGT | CTTGCCCCAG |
| 130 | 140 | 150 | 160 | 170 | 180 |
| TGCCATGACC | TTCTCGGAGA | TCCTGGACCG | TGTGGGAAGC | ATGGGCCATT | TCCAGTTCCT |
| 190 | 200 | 210 | 220 | 230 | 240 |
| GCATGTAGCC | ATACTGGGCC | TCCCGATCCT | CAACATGGCC | AACCACAACC | TGCTGCAGAT |
| 250 | 260 | 270 | 280 | 290 | 310 |
| CTTCACAGCC | GCCACCCCTG | TCCACCACTG | TCGCCCGCCC | CACAATGCCT | CCACAGGGCC |
| 310 | 320 | 330 | 340 | 350 | 360 |
| TTGGGTGCTC | CCCATGGGCC | CAAATGGGAA | GCCTGAGAGG | TGCCTCCGTT | TTGTACATCC |
| 370 | 380 | 300 | 400 | 410 | 420 |
| GCCCAATGCC | AGCCTGCCCA | ATGACACCCA | GAGGGCCATG | GAGCCATGCC | TGGATGGCTG |
| 430 | 440 | 450 | 460 | 470 | 480 |
| GGTCTACAAC | AGCACCAAGG | ACTCCATTGT | GACAGAGTGG | GACTTGGTGT | GCAACTCCAA |
| 490 | 500 | 510 | 520 | 530 | 540 |
| CAAACTGAAG | GAGATGGCCC | AGTCTATCTT | CATGGCAGGT | ATACTGATTG | GAGGGCTCGT |
| 550 | 560 | 570 | 580 | 590 | 600 |
| GCTTGGAGAC | CTGTCTGACA | GGTTTGGCCG | CAGGCCCATC | CTGACCTGCA | GCTACCTGCT |
| 610 | 620 | 630 | 640 | 650 | 660 |
| GCTGGCAGCC | AGCGGCTCCG | GTGCAGCCTT | CAGCCCCACC | TTCCCCATCT | ACATGGTCTT |
| 670 | 680 | 690 | 700 | 710 | 720 |
| CCGCTTCCTG | TGTGGCTTTG | GCATCTCAGG | CATTACCCTG | AGCACCGTCA | TCTTGAATGT |
| 730 | 740 | 750 | 760 | 770 | 780 |
| GGAATGGGTG | CCTACCCGGA | TGCGGGCCAT | CATGTCGACA | GCACTCGGGT | ACTGCTACAC |
| 790 | 800 | 810 | 820 | 830 | 840 |
| CTTTGGCCAG | TTCATTCTGC | CCGGCCTGGC | CTACGCCATC | CCCCAGTGGC | GTTGGCTGCA |
| 850 | 860 | 870 | 880 | 890 | 900 |
| GTTAACTGTG | TCCATTCCCT | TCTTCGTCTT | CTTCCTATCA | TCCTGGTGGA | CACCAGAGTC |
| 910 | 920 | 930 | 940 | 950 | 960 |
| CATACGCTGG | TTGGTCTTGT | CTGGAAAGTC | CTCGGAGGCC | CTGAAGATAC | TCCGGCGGGT |
| 970 | 980 | 950 | 1000 | 1010 | 1020 |
| GGCTGTCTTC | AATGGCAAGA | AGGAAGAGGG | AGAAAGGCTC | AGCGGGGAGG | AGCTCAAACT |
| 1030 | 1040 | 1050 | 1060 | 1070 | 1080 |
| CAACCTGCAG | AAGGAGATCT | CCTTGGCCAA | GGCCAAGTAC | ACCGCAAGTG | ACCTGTTCCG |
| 1090 | 1100 | 1110 | 1120 | 1130 | 1140 |
| GATACCCATG | CTGCGCCGCA | TGACCTTCTG | TCTTTCCCTG | GCCTGGTTTG | CTACCGGTTT |
| 1150 | 1160 | 1170 | 1180 | 1190 | 1200 |
| TGCCTACTAT | AGTTTGGCTA | TGGGTGTGGA | AGAATTTGGA | GTCAACCTCT | ACATCCTCCA |
| 1210 | 1220 | 1230 | 1240 | 1250 | 1260 |
| GATCATCTTT | GGTGGGGTCG | ATGTCCCAGC | CAAGTTCATC | ACCATCCTCT | CCTTAAGCTA |
| 1270 | 1280 | 1290 | 1300 | 1310 | 1320 |
| CCTGGGCCGG | CATACCACTC | AGGCCGCTGC | CCTGCTCCTG | GCAGGAGGGG | CCATCTTGGC |
| 1330 | 1340 | 1350 | 1360 | 1370 | 1380 |

TABLE 2-continued

Base sequence of hGAT3 cDNA

TCTCACCTTT GTGCCCTTGG ACTTGCAGAC CGTGAGGCAC GTATTGGCTG TGTTTGGGAA

```
         1390       1400       1410       1420       1430       1440
GGGATGCCTA TCCAGCTCCT TCAGCTGCCT CTTCCTCTAC ACAAGTGAAT TATACCCCAC 1450       1460       1470       1480       1490       1500
AGTCATCAGG CAAACAGGTA TGGGCGTAAG TAACCTGTGG ACCCGCGTGG GAAGCATGGT 1510       1520       1530       1540       1550       1560
GTCCCCGCTG GTGAAAATCA CGGGTGAGGT ACAGCCCTTC ATCCCCAATA TCATCTACGG 1570       1580       1590       1600       1610       1620
GATCACCGCC CTCCTCGGGG GCAGTGCTGC CCTCTTCCTG CCTGAGACCC TGAATCAGCC 1630       1640       1650       1660       1670       1680
CTTGCCAGAG ACTATCGAAG ACCTGGAAAA CTGGTCCCTG CGGGCAAAGA AGCCAAAGCA 1690       1700       1710       1720       1730       1740
GGAGCCAGAG GTGGAAAAGG CCTCCCAGAG GATCCCTCTA CAGCCTCACG GACCAGGCCT 1750       1760       1770       1780       1790       1800
GGGCTCCAGA TGAGGACAAC GGAACCCCCT TTCCCTGCCC TCCAGAGACT GATCCTAGCC 1810       1820       1830       1840       1850       1860
AGGCACCTTA GGAGTATAGG GAGGCCCCAT ATAGGTCCAT CCTCCTAGGA TGAAGCCTTC 1870       1880       1890       1900       1910       1920
TGAGAGCTTG GTGAAGGTGT CTCCATCACC ACCACCAGAG CCTCCTGCCC AGCCCTGGCC 1930       1940       1950       1960       1970       1980
AGTTCAAAGG TTCAGCCATC CCTGCCCTTG TTCTCCCTGC AACCCAGGCC CTGCCATTCT 1990       2000       2010       2020       2030       2040
TCTGTCTAGC CCTTCCCCAC TGGCCACCTT CCCCCACTGT CCCGGTCCTC TTCCCCTGAG 2050       2060       2070       2080       2090       2100
GTCCCCTGAT ATCCCCTGGC TCAGTCCTAA CAAGACTGAG TCTTAACAAG ATGAGAAGTC 2110       2120       2130       2140       2150       2160
CTCCCCTTCT TGCCTCCCGC ACTTTTCTTT GATGGGAGGT TTCAATAAAC AGCGATAAGA 2170       2180       2190       2200       2210       2220
ACTCTAAAAA AAAAAAAAA. .......... .......... .......... ..........
```

TABLE 3

Base sequence of hOAT3 amino acid

```
            133        142        151        160        169        178
ATG ACC TTC TCG GAG ATC CTG GAC CGT GTG GGA AGC ATG GGC CAT TTC CAG TTC
--- --- --- --- --- --- --- --- --- --- --- --- --- --- --- --- --- ---
Met Thr Phe Ser Glu Ile Leu Asp Arg Val Gly Ser Met Gly His Phe Gln Phe 187        196        205        214        223        232
CTG CAT GTA GCC ATA CTG GGC CTC CCG ATC CTC AAC ATG GCC AAC CAC AAC CTG
--- --- --- --- --- --- --- --- --- --- --- --- --- --- --- --- --- ---
Leu His Val Ala Ile Leu Gly Leu Pro Ile Leu Asn Met Ala Asn His Asn Leu 241        250        259        268        277        286
CTG CAG ATC TTC ACA GCC GCC ACC CCT GTC CAC CAC TGT CGC CCG CCC CAC AAT
--- --- --- --- --- --- --- --- --- --- --- --- --- --- --- --- --- ---
Leu Gln Ile Phe Thr Ala Ala Thr Pro Val His His Cys Arg Pro Pro His Asn 295        304        313        322        331        340
GCC TCC ACA GGG CCT TGG GTG CTC CCC ATG GGC CCA AAT GGG AAG CCT GAG AGG
--- --- --- --- --- --- --- --- --- --- --- --- --- --- --- --- --- ---
Ala Ser Thr Gly Pro Trp Val Leu Pro Met Gly Pro Asn Gly Lys Pro Glu Arg 349        358        367        376        385        394
TGC CTC CGT TTT GTA CAT CCG CCC AAT GCC AGC CTG CCC AAT GAC ACC CAG AGG
--- --- --- --- --- --- --- --- --- --- --- --- --- --- --- --- --- ---
Cys Leu Arg Phe Val His Pro Pro Asn Ala Ser Leu Pro Asn Asp Thr Gln Arg
```

TABLE 3-continued

Base sequence of hOAT3 amino acid

```
        403             412             421             430             439             448
GCC ATG GAG CCA TGC CTG GAT GGC TGG GTC TAC AAC AGC ACC AAG GAC TCC ATT
--- --- --- --- --- --- --- --- --- --- --- --- --- --- --- --- --- ---
Ala Met Glu Pro Cys Leu Asp Gly Trp Val Tyr Asn Ser Thr Lys Asp Ser Ile 457             466             475             484             493             502
GTG ACA GAG TGG GAC TTG GTG TGC AAC TCC AAC AAA CTG AAG GAG ATG GCC CAG
--- --- --- --- --- --- --- --- --- --- --- --- --- --- --- --- --- ---
Val Thr Glu Trp Asp Leu Val Cys Asn Ser Asn Lys Leu Lys Glu Met Ala Gln 511             520             529             538             547             556
TCT ATC TTC ATG GCA GGT ATA CTG ATT GGA GGG CTC GTG CTT GGA GAC CTG TCT
--- --- --- --- --- --- --- --- --- --- --- --- --- --- --- --- --- ---
Ser Ile Phe Met Ala Gly Ile Leu Ile Gly Gly Leu Val Leu Gly Asp Leu Ser 565             574             583             592             601             610
GAC AGG TTT GGC CGC AGG CCC ATC CTG ACC TGC AGC TAC CTG CTG CTG GCA GCC
--- --- --- --- --- --- --- --- --- --- --- --- --- --- --- --- --- ---
Asp Arg Phe Gly Arg Arg Pro Ile Leu Thr Cys Ser Tyr Leu Leu Leu Ala Ala 619             628             637             646             655             664
AGC GGC TCC GGT GCA GCC TTC AGC CCC ACC TTC CCC ATC TAC ATG GTC TTC CGC
--- --- --- --- --- --- --- --- --- --- --- --- --- --- --- --- --- ---
Ser Gly Ser Gly Ala Ala Phe Ser Pro Thr Phe Pro Ile Tyr Met Val Phe Arg 673             682             691             700             709             718
TTC CTG TGT GGC TTT GGC ATC TCA GGC ATT ACC CTG AGC ACC GTC ATC TTG AAT
--- --- --- --- --- --- --- --- --- --- --- --- --- --- --- --- --- ---
Phe Leu Cys Gly Phe Gly Ile Ser Gly Ile Thr Leu Ser Thr Val Ile Leu Asn 727             736             745             754             763             772
GTG GAA TGG GTG CCT ACC CGG ATG CGG GCC ATC ATG TCG ACA GCA CTC GGG TAC
--- --- --- --- --- --- --- --- --- --- --- --- --- --- --- --- --- ---
Val Glu Trp Val Pro Thr Arg Met Arg Ala Ile Met Ser Thr Ala Leu Gly Tyr 781             790             799             808             817             826
TGC TAC ACC TTT GGC CAG TTC ATT CTG CCC GGC CTG GCC TAC GCC ATC CCC CAG
--- --- --- --- --- --- --- --- --- --- --- --- --- --- --- --- --- ---
Cys Tyr Thr Phe Gly Gln Phe Ile Leu Pro Gly Leu Ala Tyr Ala Ile Pro Gln 835             844             853             862             871             880
TGG CGT TGG CTG CAG TTA ACT GTG TCC ATT CCC TTC TTC GTC TTC TTC CTA TCA
--- --- --- --- --- --- --- --- --- --- --- --- --- --- --- --- --- ---
Trp Arg Trp Leu Gln Leu Thr Val Ser Ile Pro Phe Phe Val Phe Phe Leu Ser 889             898             907             916             925             934
TCC TGG TGG ACA CCA GAG TCC ATA CGC TGG TTG GTC TTG TCT GGA AAG TCC TCG
--- --- --- --- --- --- --- --- --- --- --- --- --- --- --- --- --- ---
Ser Trp Trp Thr Pro Glu Ser Ile Arg Trp Leu Val Leu Ser Gly Lys Ser Ser 943             952             961             970             979             988
GAG GCC CTG AAG ATA CTC CGG CGG GTG GCT GTC TTC AAT GGC AAG AAG GAA GAG
--- --- --- --- --- --- --- --- --- --- --- --- --- --- --- --- --- ---
Glu Ala Leu Lys Ile Leu Arg Arg Val Ala Val Phe Asn Gly Lys Lys Glu Glu 997            1006            1015            1024            1033            1042
GGA GAA AGG CTC AGC TTG GAG GAG CTC AAA CTC AAC CTG CAG AAG GAG ATC TCC
--- --- --- --- --- --- --- --- --- --- --- --- --- --- --- --- --- ---
Gly Glu Arg Leu Ser Leu Glu Glu Leu Lys Leu Asn Leu Gln Lys Glu Ile Ser 1051            1060            1069            1078            1087            1096
TTG GCC AAG GCC AAG TAC ACC GCA AGT GAC CTG TTC CGG ATA CCC ATG CTG CGC
--- --- --- --- --- --- --- --- --- --- --- --- --- --- --- --- --- ---
Leu Ala Lys Ala Lys Tyr Thr Ala Ser Asp Leu Phe Arg Ile Pro Met Leu Arg 1105            1114            1123            1132            1141            1150
CGC ATG ACC TTC TGT CTT TCC CTG GCC TGG TTT GCT ACC GGT TTT GCC TAC TAT
--- --- --- --- --- --- --- --- --- --- --- --- --- --- --- --- --- ---
Arg Met Thr Phe Cys Leu Ser Leu Ala Trp Phe Ala Thr Gly Phe Ala Tyr Tyr 1159            1168            1177            1186            1195            1204
AGT TTG GCT ATG GGT GTG GAA GAA TTT GGA GTC AAC CTC TAC ATC CTC CAG ATC
--- --- --- --- --- --- --- --- --- --- --- --- --- --- --- --- --- ---
Ser Leu Ala Met Gly Val Glu Glu Phe Gly Val Asn Leu Tyr Ile Leu Gln Ile
```

TABLE 3-continued

Base sequence of hOAT3 amino acid

```
       1213        1222        1231        1240        1249        1258
ATC TTT GGT GGG GTC GAT GTC CCA GCC AAG TTC ATC ACC ATC CTC TCC TTA AGC
--- --- --- --- --- --- --- --- --- --- --- --- --- --- --- --- --- ---
Ile Phe Gly Gly Val Asp Val Pro Ala Lys Phe Ile Thr Ile Leu Ser Leu Ser 1267        1276        1285        1294        1303        1312
TAC CTG GGC CGG CAT ACC ACT CAG GCC GCT GCC CTG CTC CTG GCA GGA GGG GCC
--- --- --- --- --- --- --- --- --- --- --- --- --- --- --- --- --- ---
Tyr Leu Gly Arg His Thr Thr Gln Ala Ala Ala Leu Leu Leu Ala Gly Gly Ala 1321        1330        1339        1348        1357        1366
ATC TTG GCT CTC ACC TTT GTG CCC TTG GAC TTG CAG ACC GTG AGG ACA GTA TTG
--- --- --- --- --- --- --- --- --- --- --- --- --- --- --- --- --- ---
Ile Leu Ala Leu Thr Phe Val Pro Leu Asp Leu Gln Thr Val Arg Thr Val Leu 1375        1384        1393        1402        1411        1420
OCT GTG TTT GGG AAG GGA TGC CTA TCC AGC TCC TTC AGC TGC CTC TTC CTC TAC
--- --- --- --- --- --- --- --- --- --- --- --- --- --- --- --- --- ---
Ala Val Pho Gly Lys Gly Cys Lou Ser Ser Ser Pho Ser Cys Leu Pho Leu Tyr 1429        1436        1447        1456        1465        1474
ACA AGT GAA TTA TAC CCC ACA GTC ATC AGG CAA ACA GGT ATG GGC GTA AGT AAC
--- --- --- --- --- --- --- --- --- --- --- --- --- --- --- --- --- ---
Thr Ser Glu Lau Tyr Pro Thr Val Ile Arg Gln Thr Gly Met Gly Val Ser Asn 1483        1492        1501        1310        1519        1528
CTG TGG ACC CGC GTG GGA AGC ATG GTC TCC CCG CTG GTG AAA ATC ACG GGT GAG
--- --- --- --- --- --- --- --- --- --- --- --- --- --- --- --- --- ---
Leu Trp Thr Arg Val Gly Ser Met Val Ser Pro Leu Val Lys Ile Thr Gly Glu 1537        1546        1555        1564        1573        1982
GTA CAG CCC TTC ATC CCC AAT ATC ATC TAC GGG ATC ACC GCC CTC CTC GGG GGC
--- --- --- --- --- --- --- --- --- --- --- --- --- --- --- --- --- ---
Val Gln Pro Pho Ile Pro Asn Ile Ile Tyr Gly Ile Thr Ala Leu Leu Gly Gly 1591        1600        1609        1618        1627        1636
AGT GCT GCC CTC TTC CTG CCT GAG ACC CTG AAT CAG CCC TTG CCA GAG ACT ATC
--- --- --- --- --- --- --- --- --- --- --- --- --- --- --- --- --- ---
Ser Ala Ala Leu Phe Leu Pro Glu Thr Leu Asn Gln Pro Leu Pro Glu Thr Ile 1645        1654        1663        1672        1681        1690
GAA GAC CTG GAA AAC TGG TCC CTG CGG GCA AAG AAG CCA AAG CAG GAG CCA GAG
--- --- --- --- --- --- --- --- --- --- --- --- --- --- --- --- --- ---
Glu Asp Leu Glu Asn Trp Ser Leu Arg Ala Lys Lys Pro Lys Gln Glu Pro Glu 1699        1708        1717        1726        1736        1744
GTG GAA AAG GCC TCC CAG AGG ATC CCT CTA CAG CCT CAC GGA CCA GGC CTG GGC
--- --- --- --- --- --- --- --- --- --- --- --- --- --- --- --- --- ---
Val Glu Lys Ala Ser Gln Arg Ile Pro Leu Gln Pro His Gly Pro Gly Leu Gly

1753
TCC AGC TGA 3'
--- --- ---
Ser Ser ***
```

EXAMPLE 6

Identification of hOAT3 function

By using T7 RNA polymerase, cRNA (RNA complementary to cDNA) was prepared in vitro from the plasmid comprising the hOAT3 recovered above by the method by Sekine, et al. (see Sekine, T., et al. J. Biol. Chem., Vol. 272, pp. 18526-9, 1997).

According to the already reported method of Sekine, et al. (Sekine, T., et al. J. Biol. Chem., Vol. 272, pp. 18526-9, 1997), the resulting hOAT3 cRNA was injected in the *Xenopus oocyte*; the oocyte was subjected to an uptake test with various radiolabeled organic anions and organic cations. The control oocyte cell (oocyte cell with no injection of hOAT3 cRNA) and the oocyte cell injected with hOAT3 cRNA were cultured in a buffer containing the following radiolabels for one hour, to assay the uptake of the radiolabels into the oocytes.

Figure 6:
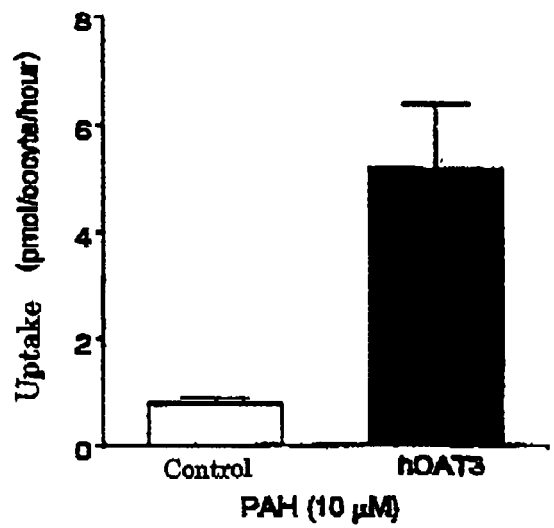
FIG. 6 depicts the uptake activity of $^{14}$C-PAH (p-aminohippuric acid) when the inventive hOAT3 was expressed in *Xenopus* oocyte.
Figure 7:
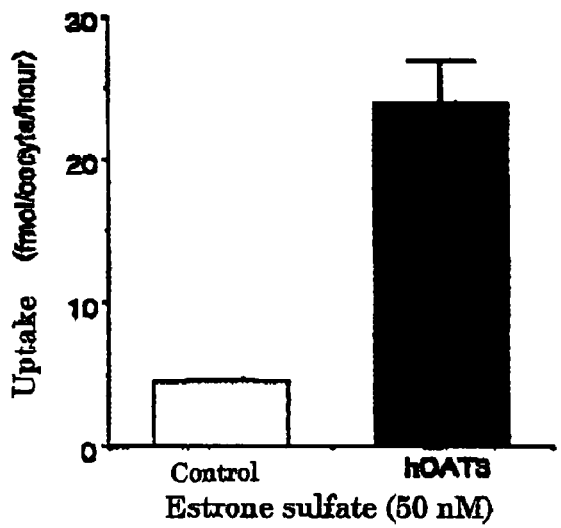
FIG. 7 depicts the uptake activity of $^{3}$H-estrone sulfate when the inventive hOAT3 was expressed in *Xenopus* oocyte.
Figure 8:
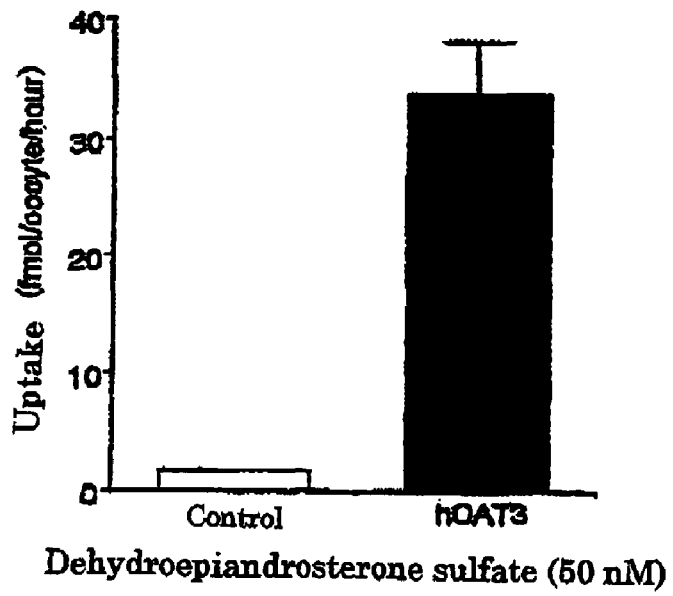
FIG. 8 depicts the uptake activity of $^{3}$H-dehydroepiandrosterone sulfate when the inventive hOAT3 was expressed in *Xenopus* oocyte.
Figure 9:
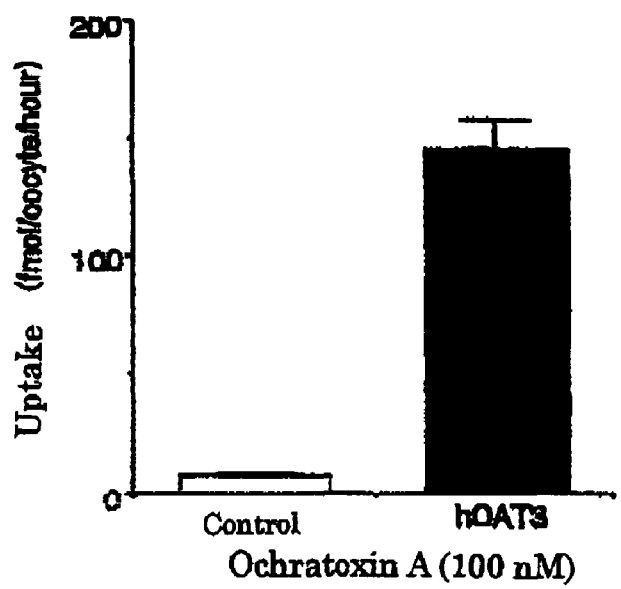
FIG. 9 depicts the uptake activity of $^{3}$H-ochratoxin A when the inventive hOAT3 was expressed in *Xenopus* oocyte.
Figure 10:
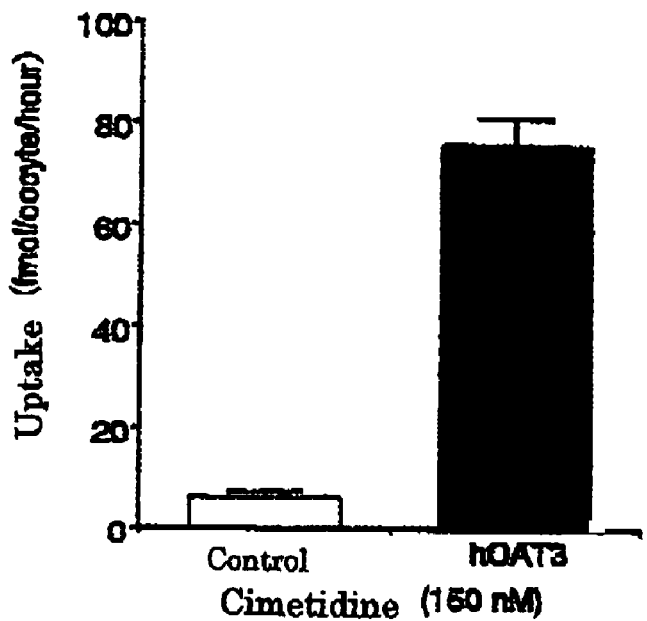
FIG. 10 depicts the uptake activity of $^{3}$H-cimetidine when the inventive hOAT3 was expressed in *Xenopus* oocyte.
Figure 11:
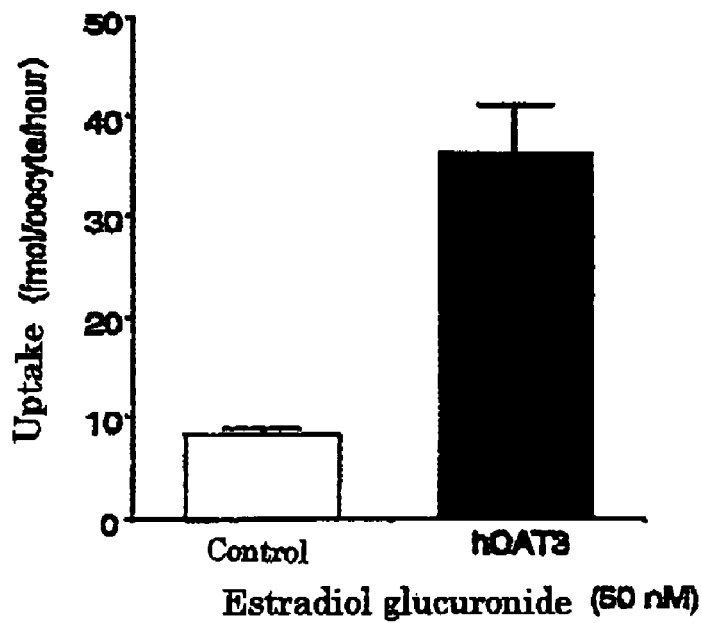
FIG. 11 depicts the uptake activity of $^{3}$H-estradiol glucuronide when the inventive hOAT3 was expressed in *Xenopus* oocyte.
Figure 12:
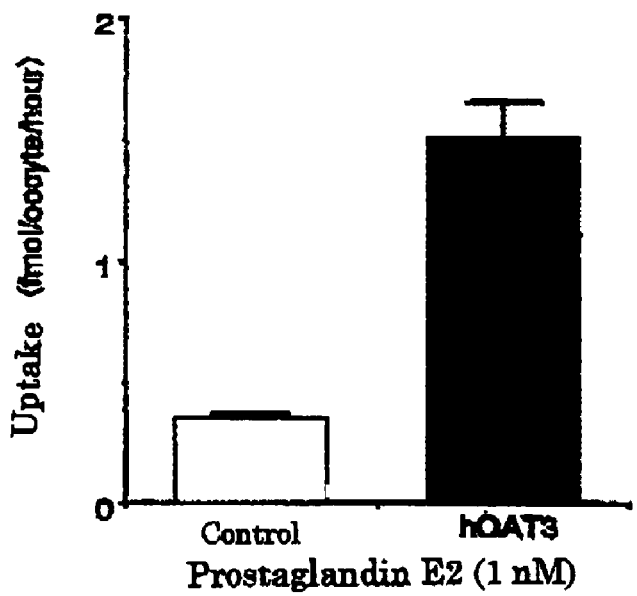
FIG. 12 depicts the uptake activity of $^{3}$H-prostaglandin E2 when the inventive hOAT3 was expressed in *Xenopus* oocyte.
Figure 13:
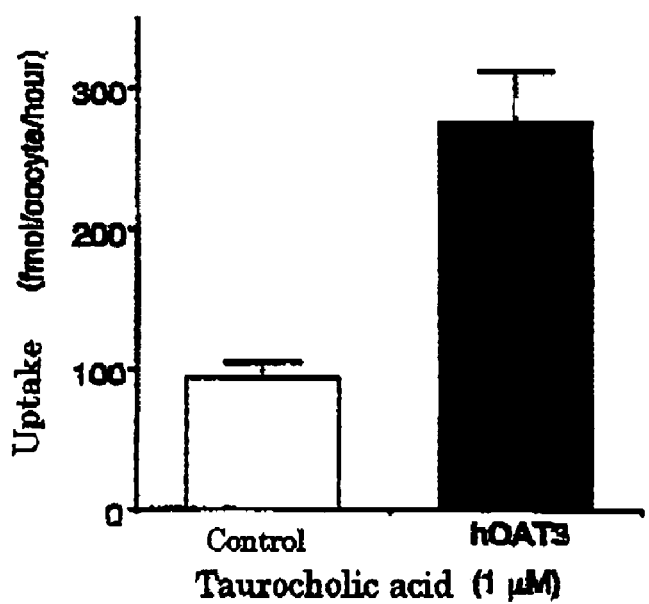
FIG. 13 depicts the uptake activity of $^{14}$C-taurocholic acid when the inventive hOAT3 was expressed in *Xenopus* oocyte.
Figure 14:
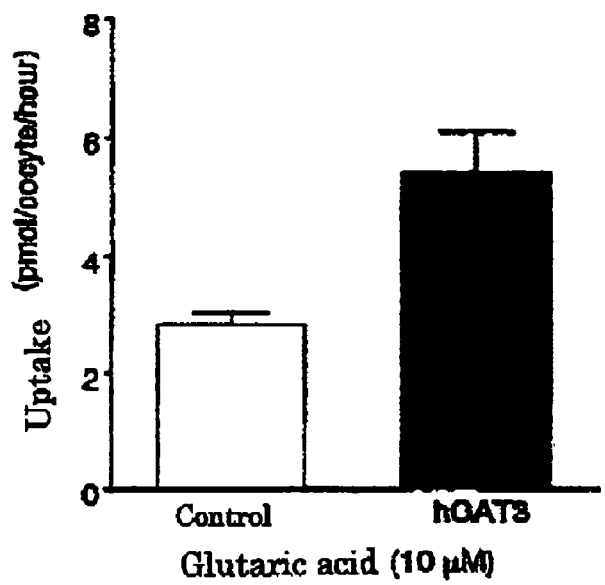
FIG. 14 depicts the uptake activity of $^{14}$C-glutaric acid when the inventive hOAT3 was expressed in *Xenopus* oocyte.
Figure 15:
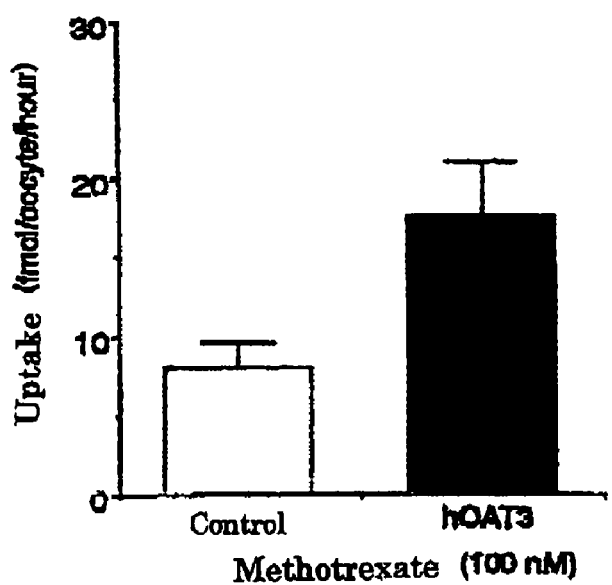
FIG. 15 depicts the uptake activity of $^{3}$H-methotrexate when the inventive hOAT3 was expressed in *Xenopus* oocyte.
Figure 16:
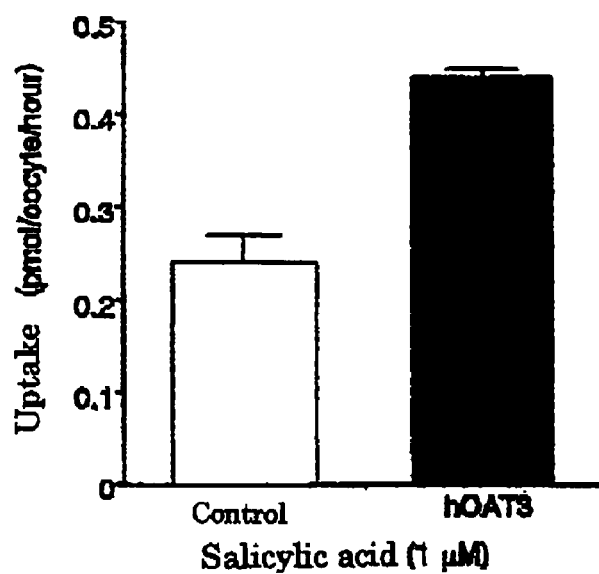
FIG. 16 depicts the uptake activity of $^{14}$C-salicylic acid when the inventive hOAT3 was expressed in *Xenopus* oocyte.
Figure 17:
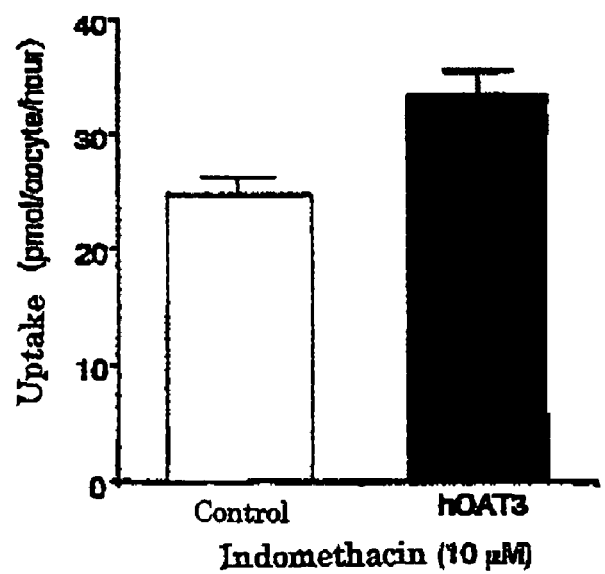
FIG. 17 depicts the uptake activity of $^{14}$C-indomethacin when the inventive hOAT3 was expressed in *Xenopus* oocyte.
Figure 18:
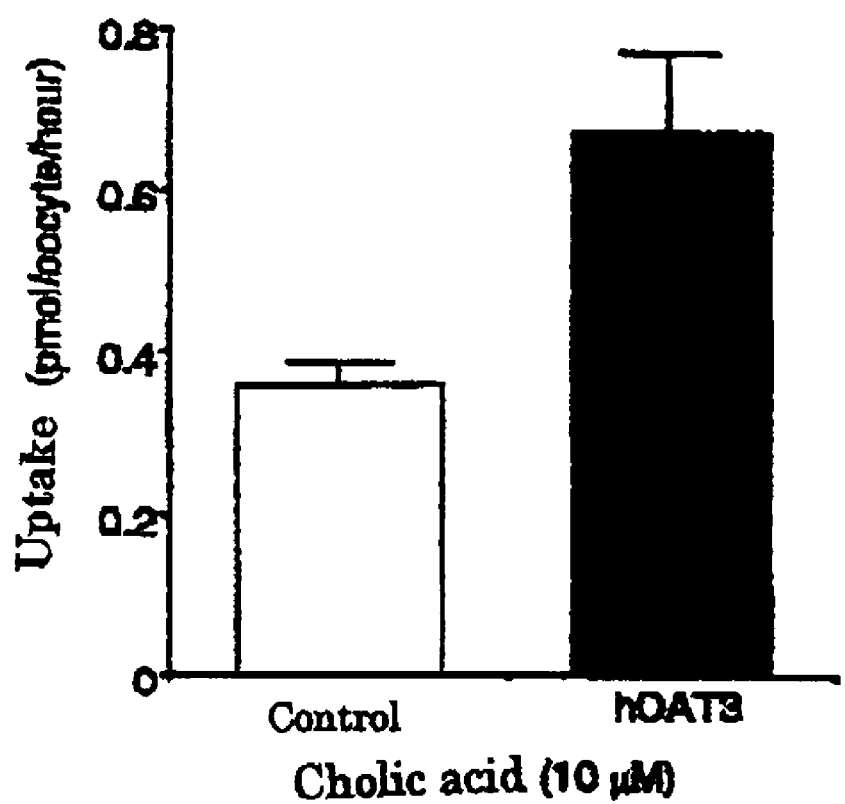
FIG. 18 depicts the uptake activity of $^{14}$C-cholic acid when the inventive hOAT3 was expressed in *Xenopus* oocyte.

The results are shown in FIGS. 6 to 18. In each figure, open column expresses the case of the control oocyte used; and closed column expresses the case of the oocyte injected with hOAT3 cRNA. FIG. 6 depicts the uptake activity of $^{14}$C-PAH (p-aminohippuric acid) (10 μM); FIG. 7 depicts the uptake activity of $^{3}$H-estrone sulfate (50 nM); FIG. 8 depicts the uptake activity of $^{3}$H-dehydroepiandrosterone sulfate (50 nM); FIG. 9 depicts the uptake activity of $^{3}$H-ochratoxin A (100 nM); FIG. 10 depicts the uptake activity of $^{3}$H-cimetidine (150 nM); FIG. 11 depicts the uptake activity of $^{3}$H-estradiol glucuronide (50 nM); FIG. 12 depicts the uptake activity of $^{3}$H-prostaglandin E2 (1 nM); FIG. 13 depicts the uptake activity of $^{14}$C-taurocholic acid (10 μM); FIG. 14 depicts the uptake activity of $^{14}$C-glutaric acid (10 μM); FIG. 15 depicts the uptake activity of $^{3}$-methotrexate (100 nM); FIG. 16 depicts the uptake activity of $^{14}$C-salicylic acid (1 μM); FIG. 17 depicts the uptake activity of $^{14}$C-indomethacin (10 μM); and FIG. 18 depicts the uptake activity of $^{14}$C-cholic acid (10 μM).

As shown in these figures, the values of these radiolabels in the oocyte with hOAT3 expression were higher than the values thereof in the control oocyte, suggesting that hOAT3 transported these compounds.

Consequently, the oocyte with hOAT3 expression takes up $^{14}$C-PAH (p-aminohippuric acid), $^3$H-estrone sulfate, $^3$H-dehydroepiandrosterone sulfate, $^3$H-ochratoxin A, $^3$H-cimetidine, $^3$H-estradiol glucuronide, $^3$H-prostaglandin E2, $^{14}$C-taurocholic acid, $^{14}$C-glutaric acid, $^3$H-methotrexate, $^{14}$C-salicylic acid, $^{14}$C-indomethacin, and $^{14}$C-cholic acid. On contrast, hOAT3 never transported the typical organic cation $^{14}$C-TEA (tetraethylammonium) (not shown in the figures).

Then, the hOAT3 transport of organic anions was examined at the Michaelis-Menten kinetic test. By examining the change in the hOAT3 uptake of estrone sulfate and methotrexate at various concentrations, the dependency of the OAT3 transport on the concentrations of these substances was examined. The uptake experiment of radiolabeled estrone sulfate and methotrexate was carried out by using the oocyte injected with hOAT3 cRNA and the control oocyte (with no injection of cRNA), by the method described above. Consequently, the Km values of estrone sulfate and methotrexate were 3.08 μM and 2.22 μM, respectively.

So as to examine the substrate selectivity of hOAT3, various anionic substances were added to the $^3$H-estrone sulfate uptake experiment system with the oocyte injected with hOAT3 cRNA, to examine their influences (inhibition experiment).

The $^3$H-estrone sulfate uptake experiment was conducted by using the oocyte injected with hOAT3 cRNA according to the method described above.

More specifically, the control oocyte (oocyte with no injection of hOAT3 cRNA) and the oocyte with injection of hOAT3 cRNA were cultured in a buffer containing 50 nM $^3$H-estrone sulfate alone or containing non-radiolabeled compounds at 500 μM or the concentration shown in the figure for one hour, to assay the uptake of $^3$H-estrone sulfate. When the uptake of 50 nM $^3$H-estrone sulfate singly contained in the buffer into the oocyte with injection of hOAT3 cRNA was designated 100%, the individual uptake values in the buffer containing inhibitory agents were expressed in %.

Figure 19:
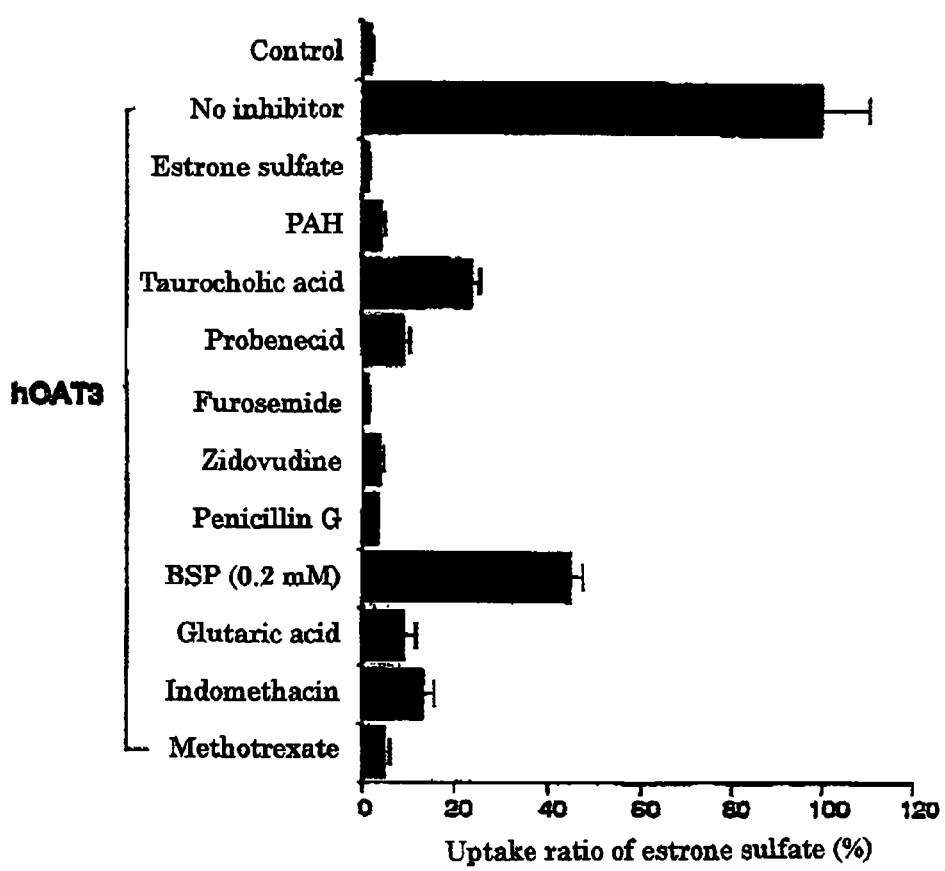
FIG. 19 depicts the results on the inhibition of the transport of $^{3}$H-estrone sulfate with the inventive hOAT3 by various organic substances.

The results are shown in FIG. 19. As shown in FIG. 19, all these compounds inhibited the uptake of $^3$H-estrone sulfate into the oocyte injected with hOAT3 cRNA, indicating that these compounds were interactive with hOAT3. Consequently, it was indicated that various anionic substances (estrone sulfate, PAH, taurocholic acid, probenecid, furosemide, zidovudine, penicillin G, BSP, glutaric acid, indomethacin, and methotrexate) significantly inhibited the transport of $^3$H-estrone sulfate with hOAT3 (see FIG. 19). Alternatively, tetraethylammonium as one of typical organic cations never exerted any inhibitory action. Based on these results, it is evidenced that the inventive hOAT3 is a multi-selective organic anion transporter.

Industrial Applicability

The invention provides a novel organic anion transporter with wide substrate selectivity of organic anions and in selective distribution in brain and liver and the like.

The inventive organic anion transporter is involved in the uptake of various drugs in cells and is also involved in the dynamics of drugs in biological organisms. Therefore, the inventive organic anion transporter is useful not only for the cell viability and activation but also for the screening of pharmacokinetics.

The invention claimed is:

1. An isolated protein comprising the amino acid sequence represented by SEQ ID NO: 2 or SEQ ID NO: 4.

* * * * *

SEQUENCE LISTING

```
<160> NUMBER OF SEQ ID NOS: 4

<210> SEQ ID NO 1
<211> LENGTH: 2179
<212> TYPE: DNA
<213> ORGANISM: Homo sapiens

<400> SEQUENCE: 1
ctgagctgcc ctactacagc agctgccggc ccctaggaca gagcagggac ctcaactaca      60
ctgatcacca gccccatcgg atccagaccc ggccaccagc tctggctcgt cttgccccag     120
tgccatgacc ttctcggaga tcctggaccg tgtgggaagc atgggccatt tccagttcct     180
gcatgtagcc atactgggcc tcccgatcct caacatggcc aaccacaacc tgctgcagat     240
cttcacagcc gccacccctg tccaccactg tcgcccgccc cacaatgcct ccacagggcc     300
ttgggtgctc cccatgggcc caaatgggaa gcctgagagg tgcctccgtt ttgtacatcc     360
gcccaatgcc agcctgccca atgacaccca gagggccatg gagccatgcc tggatggctg     420
ggtctacaac agcaccaagg actccattgt gacagagtgg gacttggtgt gcaactccaa     480
caaactgaag gagatggccc agtctatctt catggcaggt atactgattg gagggctcgt     540
gcttggagac ctgtctgaca ggtttggccg caggcccatc ctgacctgca gctacctgct     600
gctggcagcc agcggctccg gtgcagcctt cagcccacc ttccccatct acatggtctt     660
ccgcttcctg tgtggctttg gcatctcagg cattaccctg agcacgtca tcttgaatgt     720 ggaatgggtg cctacccgga tgcgggccat catgtcgaca gcactcgggt actgctacac     780
ctttggccag ttcattctgc ccggcctggc ctacgccatc cccagtggc gttggctgca     840
```

```
gttaactgtg tccattccct tcttcgtctt cttcctatca tcctggtgga caccagagtc    900
catacgctgg ttggtcttgt ctggaaagtc ctcggaggcc ctgaagatac tccggcgggt    960
ggctgtcttc aatggcaaga aggaagaggg agaaaggctc agcttggagg agctcaaact   1020
caacctgcag aaggagatct ccttggccaa ggccaagtac accgcaagtg acctgttccg   1080
gatacccatg ctgcgccgca tgaccttctg tctttccctg gctggtttg ctaccggttt   1140
tgcctactat agtttggcta tgggtgtgga agaatttgga gtcaacctct acatcctcca   1200
gatcatcttt ggtggggtgc atgtcccagc caagttcatc accatcctct ccttaagcta   1260
cctgggccgg cataccactc aggccgctgc cctgctcctg gcaggagggg ccatcttggc   1320
tctcaccttt gtgcccttgg acttgcagac cgtgaggaca gtattggctg tgtttgggaa   1380
gggatgccta tccagctcct tcagctgcct cttcctctac acaagtgaat tatacccccac  1440
agtcatcagg caaacaggta tgggcgtaag taacctgtgg accgcgtgg gaagcatggt   1500
gtccccgctg gtgaaaatca cgggtgaggt acagcccttc atccccaata tcatctacgg   1560
gatcaccgcc ctcctcgggg gcagtgctgc cctcttcctg cctgagaccc tgaatcagcc   1620
cttgccagag actatcgaag acctggaaaa ctggtccctg cgggcaaaga agccaaagca   1680
ggagccagag gtggaaaagg cctcccagag gatccctcta cagcctcacg gaccaggcct   1740
gggctccagc tgaggacaac ggaaccccct ttccctgccc tccagagact gatcctagcc   1800
aggcaccta ggagtatagg gaggccccat ataggtccat cctcctagga tgaagccttc   1860
tgagagcttg gtgaaggtgt ctccatcacc accaccagag cctcctgccc agccctggcc   1920
agttcaaagg ttcagccatc cctgcccttg ttctccctgc aacccaggcc ctgccattct   1980
tctgtctagc cctccccac tggccacctt cccccactgt cccggtcctc ttcccctgag   2040
gtcccctgat atccctggc tcagtcctaa caagactgag tcttaacaag atgagaagtc   2100
ctccccttct tgcctcccac acttttcttt gatgggaggt ttcaataaac agcgataaga   2160
actctaaaaa aaaaaaaaa                                               2179
```

<210> SEQ ID NO 2
<211> LENGTH: 542
<212> TYPE: PRT
<213> ORGANISM: Homo sapiens

<400> SEQUENCE: 2

```
Met Thr Phe Ser Glu Ile Leu Asp Arg Val Gly Ser Met Gly His Phe
  1               5                  10                  15

Gln Phe Leu His Val Ala Ile Leu Gly Leu Pro Ile Leu Asn Met Ala
             20                  25                  30

Asn His Asn Leu Leu Gln Ile Phe Thr Ala Ala Thr Pro Val His His
         35                  40                  45

Cys Arg Pro Pro His Asn Ala Ser Thr Gly Pro Trp Val Leu Pro Met
     50                  55                  60

Gly Pro Asn Gly Lys Pro Glu Arg Cys Leu Arg Phe Val His Pro Pro
 65                  70                  75                  80

Asn Ala Ser Leu Pro Asn Asp Thr Gln Arg Ala Met Glu Pro Cys Leu
                 85                  90                  95

Asp Gly Trp Val Tyr Asn Ser Thr Lys Asp Ser Ile Val Thr Glu Trp
            100                 105                 110

Asp Leu Val Cys Asn Ser Asn Lys Leu Lys Glu Met Ala Gln Ser Ile
        115                 120                 125

Phe Met Ala Gly Ile Leu Ile Gly Gly Leu Val Leu Gly Asp Leu Ser
```

```
            130                 135                 140
Asp Arg Phe Gly Arg Arg Pro Ile Leu Thr Cys Ser Tyr Leu Leu Leu
145                 150                 155                 160

Ala Ala Ser Gly Ser Gly Ala Ala Phe Ser Pro Thr Phe Pro Ile Tyr
                165                 170                 175

Met Val Phe Arg Phe Leu Cys Gly Phe Gly Ile Ser Gly Ile Thr Leu
                180                 185                 190

Ser Thr Val Ile Leu Asn Val Glu Trp Val Pro Thr Arg Met Arg Ala
                195                 200                 205

Ile Met Ser Thr Ala Leu Gly Tyr Cys Tyr Thr Phe Gly Gln Phe Ile
            210                 215                 220

Leu Pro Gly Leu Ala Tyr Ala Ile Pro Gln Trp Arg Trp Leu Gln Leu
225                 230                 235                 240

Thr Val Ser Ile Pro Phe Val Phe Phe Leu Ser Ser Trp Trp Pro Thr
                245                 250                 255

Pro Glu Ser Ile Arg Trp Leu Val Leu Ser Gly Lys Ser Ser Glu Ala
                260                 265                 270

Leu Lys Ile Leu Arg Arg Val Ala Val Phe Asn Gly Lys Lys Glu Glu
            275                 280                 285

Gly Glu Arg Leu Ser Leu Glu Glu Leu Lys Leu Asn Leu Gln Lys Glu
        290                 295                 300

Ile Ser Leu Ala Lys Ala Lys Tyr Thr Ala Ser Asp Leu Phe Arg Ile
305                 310                 315                 320

Pro Met Leu Arg Arg Met Thr Phe Cys Leu Ser Leu Ala Trp Phe Ala
                325                 330                 335

Thr Gly Phe Ala Tyr Tyr Ser Leu Ala Met Gly Val Glu Glu Phe Gly
                340                 345                 350

Val Asn Leu Tyr Ile Leu Gln Ile Ile Phe Gly Gly Val His Val Pro
            355                 360                 365

Ala Lys Phe Ile Thr Ile Leu Ser Leu Ser Tyr Leu Gly Arg His Thr
        370                 375                 380

Thr Gln Ala Ala Ala Leu Leu Leu Ala Gly Gly Ala Ile Leu Ala Leu
385                 390                 395                 400

Thr Phe Val Pro Leu Asp Leu Gln Thr Val Arg Thr Val Leu Ala Val
                405                 410                 415

Phe Gly Lys Gly Cys Leu Ser Ser Ser Phe Ser Cys Leu Phe Leu Tyr
                420                 425                 430

Thr Ser Glu Leu Tyr Pro Thr Val Ile Arg Gln Thr Gly Met Gly Val
            435                 440                 445

Ser Asn Leu Trp Thr Arg Val Gly Ser Met Val Ser Pro Leu Val Lys
450                 455                 460

Ile Thr Gly Glu Val Gln Pro Phe Ile Pro Asn Ile Ile Tyr Gly Ile
465                 470                 475                 480

Thr Ala Leu Leu Gly Gly Ser Ala Ala Leu Phe Leu Pro Glu Thr Leu
                485                 490                 495

Asn Gln Pro Leu Pro Glu Thr Ile Glu Asp Leu Glu Asn Trp Ser Leu
                500                 505                 510

Arg Ala Lys Lys Pro Lys Gln Glu Pro Glu Val Glu Lys Ala Ser Gln
            515                 520                 525

Arg Ile Pro Leu Gln Pro His Gly Pro Gly Leu Gly Ser Ser
        530                 535                 540

<210> SEQ ID NO 3
<211> LENGTH: 2191
```

<212> TYPE: DNA
<213> ORGANISM: Rattus sp.

<400> SEQUENCE: 3

```
ctgagctgtc ctaccacagc agccgccgga ccctaggaca gagcacgggc caccgccgca      60
tccacctcca gtccaactgg atccagctcc aaccaccagt tttggttcat cttgcctggt     120
gccatgacct tctccgagat tctggaccgt gtcggaagca tgggcccctt ccagtacctg     180
catgtgacct tgctggccct cccagtcctc ggaatagcca accacaactt gctacagatc     240
ttcacagcca ccaccctgt ccaccactgt cgcccgcccc caacgcctc tatagggccc       300
tgggtactcc ccttggaccc aaatgggaag cctgagaagt gtctccgctt cgtacatctg     360
ccaaatgcca gtcttcccaa tgacacccag agggccaccg agccgtgctt ggatggctgg     420
atctacaaca gcaccagaga caccattgtg atagagtggg acttggtgtg cagctccaac     480
aaactgaagg agatgcccca gtcgatcttc atggcaggca tactggttgg aggacctgtg     540
attggagaac tgtcagacag gtttggccgc aagcctatcc tgacctggag ttatctcatg     600
ctggcagcca gcggctctgg tgctgccttc agtcccagcc tccctgtcta tatgatcttc     660
cgattcctgt gtgctgcag catctcgggc atttctctga gcaccgttat cttgaatgtg     720
gaatgggtac ccacctcgat gcgggccatc tcatcaacat ctattgggta ctgctacacc     780
attggtcagt tcattctgtc cggcctggcc tatgccattc tcagtggcg ctggctacag      840
ttaacctcgt ctgctccctt cttcatcttc tccttgttgt cctggtgggt accagagtcc     900
atacgctggc tggttctatc tggaaaatac tcaaaggccc tgaagacact caacggggtg     960
gctaccttca cggcaagaa ggaggaaggg aaaaagctca ccatagagga gctgaagttc    1020
aacttgcaga aggacatcac ctcagccaag gtcaaatatg gcttatctga cttgttccgg    1080
gtgtccatcc ttcgtcgtgt gaccttctgt ctctctctgg cctggttttc tactggtttt    1140
gcctactaca gtttggctat gggggtagaa gaatttggag tcaacatcta catactccag    1200
attatctttg gtgggttga catcccagcc aagttcatca caatcctctc cttaagttat    1260
ctgggccggc gcatcactca gagcttcctc ctgctcctag caggaggggc cattttggcc    1320
ctcatctttg tgccttcaga aatgcagctc ttgagaacag cactggctgt gtttggaaag    1380
ggatgcctat ctggctcctt cagctgcctc ttcctctaca cgagtgagct ctaccctaca    1440
gtcctcaggc aaacaggtat gggtatcagt aacgtgtggg ctcgagtagg aagtatgata    1500
gccccactgg tgaaaatcac gggtgaactg cagcccttca tccctaatgt catctttggg    1560
accacggccc tactgggagg cagtgctgcc ttctttctgc ttgagaccct caatcggccc    1620
ttaccggaga ctatcgagga catacaaaac tggcacaagc aagtccagaa acaaagcag    1680
gagtcggaag cagaaaggc atcccaaata atcccgctga agactggtgg ataggaccct    1740
agctgagaac aacagaatcc tctttcctgg ccacaagaga ctgatcccaa gcagtaccct    1800
tctggagttc cttgggcacc ttggggggttg gggaaagccc taggtgggcc catgctcttg    1860
gaacaaaaac ttctgagagt tcagtaaagg tgttctaccc tcatcacctc caccatagcc    1920
tacaacccag acccggcctg ctcacagctc tagccatagg cttcccatac tcctgcactc    1980
atcctccctg cagcccagcc ctgccattct tctgtcaacc cttgccatat tggccatttc    2040
ctccattgtc ccacctccat tttccttgag atccccttagc agttctaatg gtttcttctt    2100
accttgccca aactctctcc ttggtgggaa atttcaataa accacaatga agaactcaaa    2160
aaaaaaaaaa aaaaaaaaaa aaaaaaaaaa a                                    2191
```

<210> SEQ ID NO 4
<211> LENGTH: 536
<212> TYPE: PRT
<213> ORGANISM: Rattus sp.

<400> SEQUENCE: 4

Met Thr Phe Ser Glu Ile Leu Asp Arg Val Gly Ser Met Gly Pro Phe
1               5                   10                  15

Gln Tyr Leu His Val Thr Leu Leu Ala Leu Pro Val Leu Gly Ile Ala
            20                  25                  30

Asn His Asn Leu Leu Gln Ile Phe Thr Ala Thr Thr Pro Val His His
        35                  40                  45

Cys Arg Pro Pro Pro Asn Ala Ser Ile Gly Pro Trp Val Leu Pro Leu
    50                  55                  60

Asp Pro Asn Gly Lys Pro Glu Lys Cys Leu Arg Phe Val His Leu Pro
65                  70                  75                  80

Asn Ala Ser Leu Pro Asn Asp Thr Gln Arg Ala Thr Glu Pro Cys Leu
                85                  90                  95

Asp Gly Trp Ile Tyr Asn Ser Thr Arg Asp Thr Ile Val Ile Glu Trp
            100                 105                 110

Asp Leu Val Cys Ser Ser Asn Lys Leu Lys Glu Met Ala Gln Ser Ile
        115                 120                 125

Phe Met Ala Gly Ile Leu Val Gly Gly Pro Val Ile Gly Glu Leu Ser
130                 135                 140

Asp Arg Phe Gly Arg Lys Pro Ile Leu Thr Trp Ser Tyr Leu Met Leu
145                 150                 155                 160

Ala Ala Ser Gly Ser Gly Ala Ala Phe Ser Pro Ser Leu Pro Val Tyr
                165                 170                 175

Met Ile Phe Arg Phe Leu Cys Gly Cys Ser Ile Ser Gly Ile Ser Leu
            180                 185                 190

Ser Thr Val Ile Leu Asn Val Glu Trp Val Pro Thr Ser Met Arg Ala
        195                 200                 205

Ile Ser Ser Thr Ser Ile Gly Tyr Cys Tyr Thr Ile Gly Gln Phe Ile
    210                 215                 220

Leu Ser Gly Leu Ala Tyr Ala Ile Pro Gln Trp Arg Trp Leu Gln Leu
225                 230                 235                 240

Thr Ser Ser Ala Pro Phe Phe Ile Phe Ser Leu Leu Ser Trp Trp Val
                245                 250                 255

Pro Glu Ser Ile Arg Trp Leu Val Leu Ser Gly Lys Tyr Ser Lys Ala
            260                 265                 270

Leu Lys Thr Leu Gln Arg Val Ala Thr Phe Asn Gly Lys Lys Glu Glu
        275                 280                 285

Gly Lys Lys Leu Thr Ile Glu Glu Leu Lys Phe Asn Leu Gln Lys Asp
    290                 295                 300

Ile Thr Ser Ala Lys Val Lys Tyr Gly Leu Ser Asp Leu Phe Arg Val
305                 310                 315                 320

Ser Ile Leu Arg Arg Val Thr Phe Cys Leu Ser Leu Ala Trp Phe Ser
                325                 330                 335

Thr Gly Phe Ala Tyr Tyr Ser Leu Ala Met Gly Val Glu Glu Phe Gly
            340                 345                 350

Val Asn Ile Tyr Ile Leu Gln Ile Ile Phe Gly Gly Val Asp Ile Pro
        355                 360                 365

Ala Lys Phe Ile Thr Ile Leu Ser Leu Ser Tyr Leu Gly Arg Arg Ile
    370                 375                 380

Thr Gln Ser Phe Leu Leu Leu Leu Ala Gly Gly Ala Ile Leu Ala Leu

```
385                 390                 395                 400
Ile Phe Val Pro Ser Glu Met Gln Leu Leu Arg Thr Ala Leu Ala Val
                405                 410                 415
Phe Gly Lys Gly Cys Leu Ser Gly Ser Phe Ser Cys Leu Phe Leu Tyr
                420                 425                 430
Thr Ser Glu Leu Tyr Pro Thr Val Leu Arg Gln Thr Gly Met Gly Ile
        435                 440                 445
Ser Asn Val Trp Ala Arg Val Gly Ser Met Ile Ala Pro Leu Val Lys
        450                 455                 460
Ile Thr Gly Glu Leu Gln Pro Phe Ile Pro Asn Val Ile Phe Gly Thr
465                 470                 475                 480
Thr Ala Leu Leu Gly Gly Ser Ala Ala Phe Phe Leu Leu Glu Thr Leu
                485                 490                 495
Asn Arg Pro Leu Pro Glu Thr Ile Glu Asp Ile Gln Asn Trp His Lys
                500                 505                 510
Gln Val Gln Lys Thr Lys Gln Glu Ser Glu Ala Glu Lys Ala Ser Gln
        515                 520                 525
Ile Ile Pro Leu Lys Thr Gly Gly
        530                 535
```